(12) United States Patent
Sasaki

(10) Patent No.: US 10,923,224 B2
(45) Date of Patent: Feb. 16, 2021

(54) NON-TRANSITORY COMPUTER-READABLE RECORDING MEDIUM, SKILL DETERMINATION METHOD, SKILL DETERMINATION DEVICE AND SERVER

(71) Applicant: FUJITSU LIMITED, Kawasaki (JP)

(72) Inventor: Kazuo Sasaki, Kobe (JP)

(73) Assignee: FUJITSU LIMITED, Kawasaki (JP)

( * ) Notice: Subject to any disclaimer, the term of this patent is extended or adjusted under 35 U.S.C. 154(b) by 254 days.

(21) Appl. No.: 15/467,649

(22) Filed: Mar. 23, 2017

(65) Prior Publication Data

US 2017/0189784 A1 Jul. 6, 2017

Related U.S. Application Data

(63) Continuation of application No. PCT/JP2015/077851, filed on Sep. 30, 2015.

(30) Foreign Application Priority Data

Oct. 10, 2014 (JP) .............................. JP2014-208981

(51) Int. Cl.
*A63B 69/36* (2006.01)
*G06F 19/00* (2018.01)
(Continued)

(52) U.S. Cl.
CPC ......... *G16H 20/30* (2018.01); *A63B 69/3608* (2013.01); *A63B 69/3667* (2013.01);
(Continued)

(58) Field of Classification Search
None
See application file for complete search history.

(56) References Cited

U.S. PATENT DOCUMENTS 5,099,859 A * 3/1992 Bell ..................... A61B 5/1121
348/E5.086
5,821,417 A * 10/1998 Naruo ................ A63B 24/0003
73/491
(Continued)

FOREIGN PATENT DOCUMENTS

CN 102470267 A 5/2012
CN 103596625 A 2/2014
(Continued)

OTHER PUBLICATIONS

Partial European Search Report dated Sep. 18, 2017 in corresponding European Patent Application No. 15849229.8.
(Continued)

*Primary Examiner* — Eddy Saint-Vil
*Assistant Examiner* — William D Ermlick
(74) *Attorney, Agent, or Firm* — Staas & Halsey LLP

(57) ABSTRACT

A skill determination device determines each second frame corresponding to phase types from second frames having position information of a feature point, which corresponds to a predetermined part or a joint of a body of a second user, based on phase definition information in which a plurality of first frames having position information of a feature point corresponding to a predetermined part or a joint of a body of a first user and the phase types corresponding to the plurality of first frames, respectively, are associated with each other and determines a feature amount of a motion, an attitude, or the joint of the second user derived from the feature point included in the second frame determined for each of the phase types.

7 Claims, 32 Drawing Sheets

(51) Int. Cl.
    *A63B 71/06*     (2006.01)
    *G09B 19/00*     (2006.01)
    *G06K 9/00*     (2006.01)
    *G16H 20/30*     (2018.01)

(52) U.S. Cl.
    CPC .......... *A63B 71/06* (2013.01); *G06K 9/00342* (2013.01); *G09B 19/003* (2013.01); *G09B 19/0038* (2013.01)

(56) References Cited

U.S. PATENT DOCUMENTS

| | | | | |
|---|---|---|---|---|
| 5,947,742 | A * | 9/1999 | Katayama | A63B 24/0003 434/247 |
| 6,041,651 | A * | 3/2000 | Naruo | A63B 24/0003 73/491 |
| 6,083,123 | A * | 7/2000 | Wood | A63B 69/36 473/409 |
| 6,537,076 | B2 * | 3/2003 | McNitt | A63B 24/0003 434/247 |
| 7,264,554 | B2 * | 9/2007 | Bentley | A61B 5/1122 473/222 |
| 2002/0019258 | A1 * | 2/2002 | Kim | A63F 13/10 463/36 |
| 2003/0040380 | A1 * | 2/2003 | Wright | A63B 57/00 473/409 |
| 2004/0209698 | A1 | 10/2004 | Ueda et al. | |
| 2008/0139307 | A1 * | 6/2008 | Ueshima | A63F 13/10 463/31 |
| 2009/0148000 | A1 * | 6/2009 | Madsen | G06T 7/246 382/107 |
| 2009/0209358 | A1 * | 8/2009 | Niegowski | A43B 3/0005 473/223 |
| 2009/0220124 | A1 * | 9/2009 | Siegel | G06K 9/00342 382/103 |
| 2010/0015585 | A1 * | 1/2010 | Baker | A63B 24/0003 434/247 |
| 2010/0034462 | A1 * | 2/2010 | Nevatia | G06K 9/4642 382/190 |
| 2010/0303303 | A1 * | 12/2010 | Shen | G06K 9/00335 382/107 |
| 2010/0306712 | A1 * | 12/2010 | Snook | G06F 3/017 715/863 |
| 2011/0230274 | A1 | 9/2011 | Lafortune et al. | |
| 2012/0000300 | A1 * | 1/2012 | Sunagawa | A61B 5/1116 73/865.4 |
| 2012/0021833 | A1 * | 1/2012 | Boch | G06F 3/011 463/36 |
| 2012/0083351 | A1 | 4/2012 | Kim et al. | |
| 2012/0143358 | A1 * | 6/2012 | Adams | G06F 3/011 700/92 |
| 2012/0183940 | A1 * | 7/2012 | Aragones | G06F 19/3481 434/247 |
| 2012/0190505 | A1 * | 7/2012 | Shavit | A63B 71/0622 482/8 |
| 2012/0214594 | A1 * | 8/2012 | Kirovski | A63F 13/42 463/36 |
| 2012/0253201 | A1 * | 10/2012 | Reinhold | A61B 5/1113 600/473 |
| 2012/0327194 | A1 * | 12/2012 | Shiratori | G06K 9/00342 348/47 |
| 2013/0029791 | A1 * | 1/2013 | Rose | G09B 19/0038 473/409 |
| 2013/0123667 | A1 * | 5/2013 | Komatireddy | A61B 5/0002 600/595 |
| 2013/0171601 | A1 * | 7/2013 | Yuasa | A61B 5/1114 434/258 |
| 2013/0252216 | A1 * | 9/2013 | Clavin | G09B 19/0038 434/257 |
| 2013/0278501 | A1 * | 10/2013 | Bulzacki | G06F 3/0304 345/157 |
| 2013/0302768 | A1 * | 11/2013 | Webb | G09B 19/0038 434/247 |
| 2013/0331199 | A1 * | 12/2013 | Wright | A63B 69/3632 473/266 |
| 2014/0079290 | A1 | 3/2014 | Nakano et al. | |
| 2014/0147820 | A1 * | 5/2014 | Snow | G06F 19/3481 434/247 |
| 2014/0177926 | A1 | 6/2014 | Nojima | |
| 2014/0219550 | A1 * | 8/2014 | Popa | G06K 9/00342 382/154 |
| 2014/0282105 | A1 * | 9/2014 | Nordstrom | G06F 3/016 715/753 |
| 2014/0287389 | A1 * | 9/2014 | Kallmann | G06F 19/3481 434/247 |
| 2014/0347392 | A1 * | 11/2014 | Odessky | A61B 5/1121 345/633 |
| 2014/0364230 | A1 * | 12/2014 | Borghese | A63F 13/537 463/34 |
| 2015/0154447 | A1 * | 6/2015 | Wilson | A63F 13/211 382/103 |
| 2015/0193945 | A1 * | 7/2015 | Baek | G06F 3/011 345/474 |
| 2015/0196803 | A1 * | 7/2015 | Shavit | A63B 71/0622 482/8 |
| 2015/0324636 | A1 * | 11/2015 | Bentley | G11B 27/17 386/227 |
| 2016/0042242 | A1 * | 2/2016 | Segawa | H04N 13/128 382/103 |
| 2016/0129343 | A1 * | 5/2016 | Domansky | A63F 13/428 463/7 |
| 2016/0253710 | A1 * | 9/2016 | Publicover | H04W 4/21 705/14.66 |
| 2016/0256740 | A1 * | 9/2016 | Rowe | G06T 7/66 |
| 2017/0046568 | A1 * | 2/2017 | Bulzacki | G06F 3/0304 |
| 2017/0061818 | A1 * | 3/2017 | Hijioka | G09B 19/0038 |
| 2017/0103672 | A1 * | 4/2017 | Dey | G06F 3/0304 |
| 2019/0060752 | A1 * | 2/2019 | Lee | G06T 19/006 |
| 2020/0058148 | A1 * | 2/2020 | Blaylock | G06T 7/248 |

FOREIGN PATENT DOCUMENTS

| | | |
|---|---|---|
| CN | 103685862 A | 3/2014 |
| CN | 103888643 A | 6/2014 |
| JP | 2004-313479 | 11/2004 |
| JP | 2008-236124 | 10/2008 |
| JP | 2012-531941 | 12/2012 |
| JP | 2014-64110 | 4/2014 |
| JP | 2014-512220 | 5/2014 |
| JP | 2014-123322 | 7/2014 |
| KR | 10-2014-0012742 | 2/2014 |
| WO | WO 2011/002225 A1 | 1/2011 |
| WO | WO 2012/138536 A1 | 10/2012 |

OTHER PUBLICATIONS

Korean Office Action dated May 24, 2018 in corresponding Korean Patent Application No. 10-2017-7008866.
International Search Report dated Nov. 10, 2015 in corresponding International Application No. PCT/JP2015/077851**.
Office Action dated Jun. 28, 2018, in corresponding Chinese Patent Application No. 201580054106.2, 21 pgs.
Office Action dated Dec. 16, 2019 in corresponding European Patent Application No. 15849229.8.

* cited by examiner

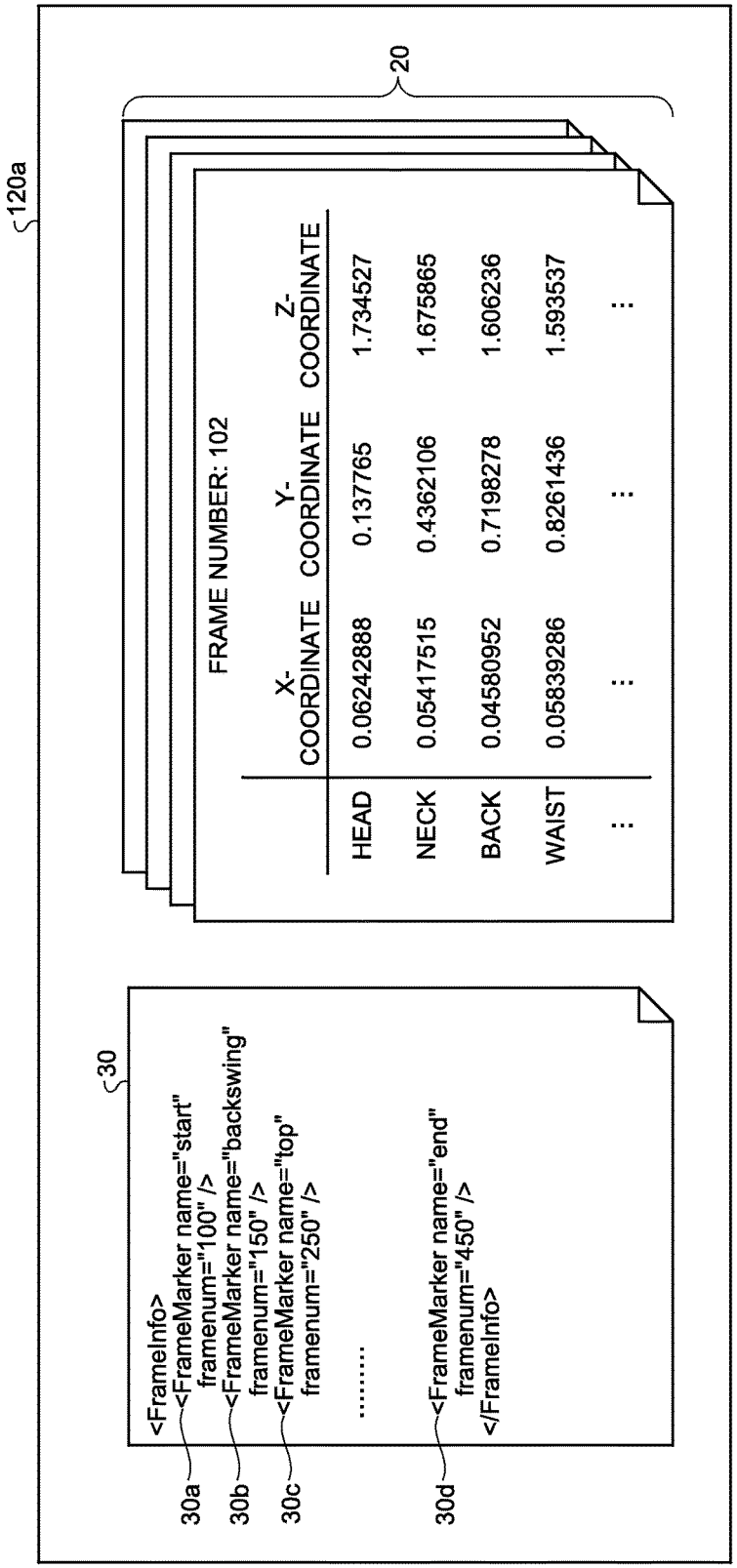

FIG.4

| MODULE NAME | SKILL DETERMINATION NAME | PARAMETER DEFINITION | | |
|---|---|---|---|---|
| | | TARGET PHASE | COMPARATIVE POSITION | REFERENCE PARAMETER |
| PositionChecker | MOVEMENT OF HEAD | start-follow | start: HEAD, current: HEAD | 8, 10, 20 |
| AngleChecker (1) | LEFT ELBOW ANGLE | start-impact | current: LEFT SHOULDER, current: LEFT ELBOW, current: LEFT WRIST | (135-180), (130-135, 180-190), (110-130, 190-200) |
| AngleChecker (2) | FORWARD INCLINED ATTITUDE | start-impact | current: HEAD, current: WAIST | (25-40), (20-25, 40-55), (8-20, 55-60) |
| ... | | | | |

| USER IDENTIFICATION INFORMATION | ITEM | SKILL DETERMINATION RESULT |
|---|---|---|
| U101 | GOLF | SKILL DETERMINATION RESULT OF USER IDENTIFICATION INFORMATION U101 |
| U102 | GOLF | SKILL DETERMINATION RESULT OF USER IDENTIFICATION INFORMATION U102 |
| U103 | BASEBALL | SKILL DETERMINATION RESULT OF USER IDENTIFICATION INFORMATION U103 |
| ... | ... | ... |

FIG.23

DATE: AUGUST 1, 2015

| PHASE | DETERMINATION RESULT OF HEAD MOVEMENT | DETERMINATION RESULT OF RIGHT ELBOW ANGLE | DETERMINATION RESULT OF FORWARD INCLINED ATTITUDE | DETERMINATION RESULT OF WAIST ROTATION |
|---|---|---|---|---|
| start | Excellent (○○ cm) | Excellent (○○°) | Excellent (○○°) | good (○○°) |
| backswing | Excellent (○○ cm) | Excellent (○○°) | Excellent (○○°) | good (○○°) |
| top | Excellent (○○ cm) | bad (○○°) | Excellent (○○°) | good (○○°) |
| impact | Excellent (○○ cm) | good (○○°) | Excellent (○○°) | bad (○○°) |
| follow | Excellent (○○ cm) | good (○○°) | Excellent (○○°) | good (○○°) |
| end | Excellent (○○ cm) | Excellent (○○°) | Excellent (○○°) | good (○○°) |

DATE: AUGUST 5, 2015

| PHASE | DETERMINATION RESULT OF HEAD MOVEMENT | DETERMINATION RESULT OF RIGHT ELBOW ANGLE | DETERMINATION RESULT OF FORWARD INCLINED ATTITUDE | DETERMINATION RESULT OF WAIST ROTATION |
|---|---|---|---|---|
| start | Excellent (○○ cm) | Excellent (○○°) | Excellent (○○°) | good (○○°) |
| backswing | Excellent (○○ cm) | Excellent (○○°) | Excellent (○○°) | good (○○°) |
| top | Excellent (○○ cm) | good (○○°) | good (○○°) | good (○○°) |
| impact | Excellent (○○ cm) | good (○○°) | Excellent (○○°) | bad (○○°) |
| follow | Excellent (○○ cm) | good (○○°) | Excellent (○○°) | good (○○°) |
| end | Excellent (○○ cm) | Excellent (○○°) | Excellent (○○°) | good (○○°) |

DATE: AUGUST 8, 2015

| PHASE | DETERMINATION RESULT OF HEAD MOVEMENT | DETERMINATION RESULT OF RIGHT ELBOW ANGLE | DETERMINATION RESULT OF FORWARD INCLINED ATTITUDE | DETERMINATION RESULT OF WAIST ROTATION |
|---|---|---|---|---|
| start | Excellent (○○ cm) | Excellent (○○°) | Excellent (○○°) | good (○○°) |
| backswing | Excellent (○○ cm) | Excellent (○○°) | Excellent (○○°) | good (○○°) |
| top | Excellent (○○ cm) | good (○○°) | Excellent (○○°) | good (○○°) |
| impact | good (○○°) | good (○○°) | Excellent (○○°) | bad (○○°) |
| follow | Excellent (○○ cm) | good (○○°) | Excellent (○○°) | good (○○°) |
| end | Excellent (○○ cm) | Excellent (○○°) | Excellent (○○°) | good (○○°) |

| USER IDENTIFICATION INFORMATION | ADDRESS | GENDER | AGE | HEIGHT | WEIGHT |
|---|---|---|---|---|---|
| U101 | XXX@ABC | MALE | 30 YEARS OLD | ○○ cm | ○○ kg |
| U102 | XXX@ABC | FEMALE | 35 YEARS OLD | ○○ cm | ○○ kg |
| U103 | XXX@ABC | MALE | 28 YEARS OLD | ○○ cm | ○○ kg |
| ... | ... | ... | ... | ... | ... |

| CONDITION | | | ADVERTISEMENT BANNER INFORMATION |
|---|---|---|---|
| ITEM | GENDER | AGE | |
| GOLF | MALE | 20 YEARS OLD OR OLDER | ADVERTISEMENT BANNER A1 (http//www.○○○○), ADVERTISEMENT BANNER B1 (http//www.○○○○), ADVERTISEMENT BANNER C1 (http//www.○○○○),··· |
| | FEMALE | 20 YEARS OLD OR OLDER | ADVERTISEMENT BANNER A2 (http//www.○○○○), ADVERTISEMENT BANNER B2 (http//www.○○○○), ADVERTISEMENT BANNER C2 (http//www.○○○○),··· |
| ... | | | ... |
| BASE-BALL | MALE | 10 YEARS OLD OR OLDER | ADVERTISEMENT BANNER X (http//www.○○○○), ADVERTISEMENT BANNER Y (http//www.○○○○), ADVERTISEMENT BANNER Z (http//www.○○○○),··· |
| ... | | | ... |

| ITEM | CONDITION | | PRODUCT NAME | COMMENT |
|---|---|---|---|---|
| | PHASE | DETERMINATION RESULT | | |
| GOLF | impact | DETERMINATION RESULT OF WAIST ROTATION: -45°±α<br>DETERMINATION RESULT OF RIGHT KNEE ANGLE: 10°±α | GOLF CLUB A | RECOMMEND SHAFT WHOSE HAND SIDE IS SOFT TO ENABLE BENDING TO BE FULLY USED AS BODY TURN TYPE |
| | impact | DETERMINATION RESULT OF WAIST ROTATION: -35°±α<br>DETERMINATION RESULT OF RIGHT KNEE ANGLE: 30°±α | GOLF CLUB B | RECOMMEND GOLF CLUB WHOSE HAND SIDE FROM MIDDLE PART OF GOLF CLUB IS HARD TO PREVENT SHAFT FROM BEING GREATLY BENT SINCE BEHAVIOR OF CLUB IS INTENSE IN WRIST RETURN TYPE |
| | ⋮ | ⋮ | ⋮ | |
| BASEBALL | | | | |
| ⋮ | | | | |

520d

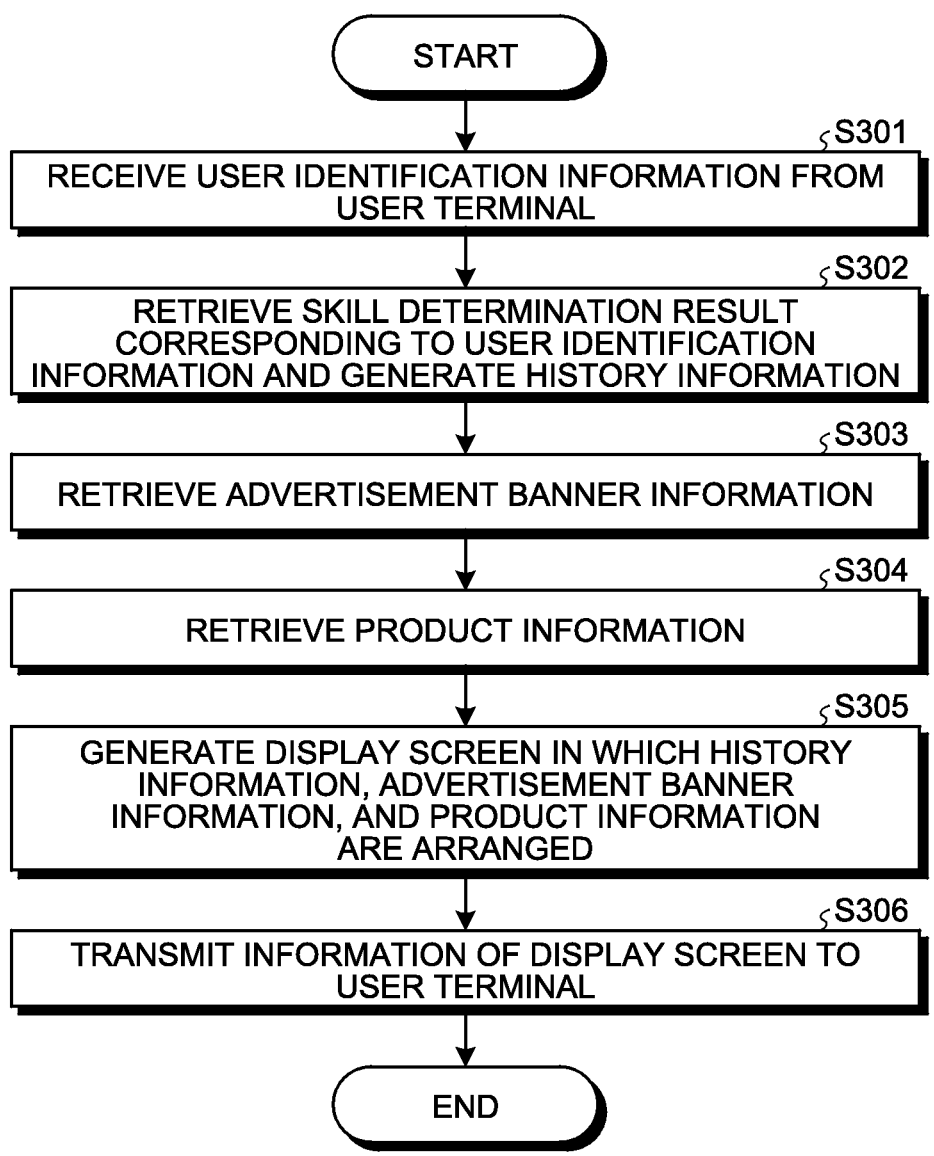

FIG.30

| USER IDENTIFI-CATION INFORMATION | ADDRESS | GENDER | AGE | HEIGHT | WEIGHT | SCHOOL | DRIVING RANGE |
|---|---|---|---|---|---|---|---|
| U101 | XXX@ABC | MALE | 30 YEARS OLD | ○○ cm | ○○ kg | SCHOOL A | DRIVING RANGE a |
| U102 | XXX@ABC | FEMALE | 35 YEARS OLD | ○○ cm | ○○ kg | SCHOOL B | DRIVING RANGE a |
| U103 | XXX@ABC | MALE | 28 YEARS OLD | ○○ cm | ○○ kg | SCHOOL A | DRIVING RANGE b |
| ... | ... | ... | ... | ... | ... | ... | ... |

| GROUP IDENTIFICATION INFORMATION | AFFILIATED USER IDENTIFICATION INFORMATION |
|---|---|
| G101 | U101, U103, U114, ... |
| G102 | U103, U122, U130, ... |
| G103 | U110, U115, U128, ... |
| ... | ... |

| EXPERT IDENTIFI-CATION INFORMATION | PROFILE INFORMATION | MODEL DATA | EVALUA-TION VALUE |
|---|---|---|---|
| C101 | PROFILE INFORMATION OF EXPERT WITH EXPERT IDENTIFICATION INFORMATION C101 | FIRST MODEL DATA | 80 |
| C102 | PROFILE INFORMATION OF EXPERT WITH EXPERT IDENTIFICATION INFORMATION C102 | FIRST MODEL DATA, SECOND MODEL DATA | 50 |
| C103 | PROFILE INFORMATION OF EXPERT WITH EXPERT IDENTIFICATION INFORMATION C103 | FIRST MODEL DATA, SECOND MODEL DATA, THIRD MODEL DATA | 70 |
| ... | ... | ... | ... |

NON-TRANSITORY COMPUTER-READABLE RECORDING MEDIUM, SKILL DETERMINATION METHOD, SKILL DETERMINATION DEVICE AND SERVER

CROSS-REFERENCE TO RELATED APPLICATION

This application is a continuation application, under 35 U.S.C. § 111(a), of International Application PCT/JP2015/077851, filed on Sep. 30, 2015, which claims foreign priority benefit to Japanese patent application No. 2014-208981, filed Oct. 10, 2014, and designating the U.S., the entire contents of which are incorporated herein by reference.

FIELD

The present invention relates to a skill determination program and the like.

BACKGROUND

A user performing training in various sports fields sometimes receive coaching from an expert. In general, the expert coaches the user using a sense or the like based on the past coaching experience. Recently, the expert sometimes also coaches the user by displaying a video obtained by shooting the user on a display and causing the user to confirm his own form.

In addition, the expert also gives the user advice by causing the user to wear an acceleration sensor, performing sensing, and referring to numerical data which is obtained from a result of the sensing during training. When the advice is given on the basis of such numerical data, it is possible to perform the coaching that makes the user convinced.

Incidentally, dedicated application software configured to evaluate a specific motion of the user by focusing on the specific motion has been sold in some popular sports. Hereinafter, the dedicated application software will be referred to as a dedicated application. The user can confirm his own skill regarding a specific skill using the above-described dedicated application even when there is no expert. For example, when a dedicated application configured to evaluate swing speed of a bat is used, the user can know his own swing speed.

Patent Literature 1: Japanese Laid-open Patent Publication No. 2004-313479
Patent Literature 2: Japanese Laid-open Patent Publication No. 2008-236124

However, the above-described related art has a general problem that it is difficult to automatically determine the user's skill.

For example, the presence of the expert is set as the major premise in the case of performing the coaching by performing the sensing of the user, and the expert sets start and end timings of the sensing and performs analysis of the numerical data, and thus, it is difficult for the user to directly and automatically use the data.

In addition, the dedicated application can be easily used directly by the user, but only enables the evaluation of content limited to some sports and lacks general versatility.

SUMMARY

According to an aspect of the embodiment of the invention, a non-transitory computer-readable recording medium stores therein a skill determination program that causes a computer to execute a process including: first determining each second frame corresponding to phase types from second frames having position information of a feature point, which corresponds to a predetermined part or a joint of a body of a second user, based on phase definition information in which a plurality of first frames having position information of a feature point corresponding to a predetermined part or a joint of a body of a first user and the phase types corresponding to the plurality of first frames, respectively, are associated with each other; and second determining a feature amount of a motion, an attitude, or the joint of the second user derived from the feature point included in the second frame determined for each of the phase types based on skill definition information defined by associating a feature amount of a motion, an attitude, or the joint of the first user derived from the feature point included in each of the plurality of first frames, a determination reference of a skill, and a phase type serving as a determination target with each other.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 3 is a diagram illustrating an example of a data structure of model data.
FIG. 4 is a diagram illustrating an example of a data structure of skill determination definition data.

FIG. 22 is a diagram illustrating an example of a data structure of a skill determination result table.

FIG. 23 is a diagram illustrating examples of a skill determination result.

FIG. 24 is a diagram illustrating an example of a data structure of a personal information table according to the second embodiment.

FIG. 25 is a diagram illustrating an example of a data structure of a banner information table.

FIG. 26 is a diagram illustrating an example of a data structure of a product table.

FIG. 27 is a flowchart illustrating a processing procedure of the server according to the second embodiment.

FIG. 30 is a diagram illustrating an example of a data structure of a personal information table according to the third embodiment.

FIG. 31 is a diagram illustrating an example of a data structure of a group management table.

FIG. 35 is a diagram illustrating an example of a data structure of an expert data table.

DESCRIPTION OF EMBODIMENTS

Hereinafter, embodiments of a skill determination program, a skill determination method, a skill determination device, and a server disclosed in the present application will be described in detail with reference to the drawings. Incidentally, the invention is not limited to the embodiments.

First Embodiment

Figure 1:
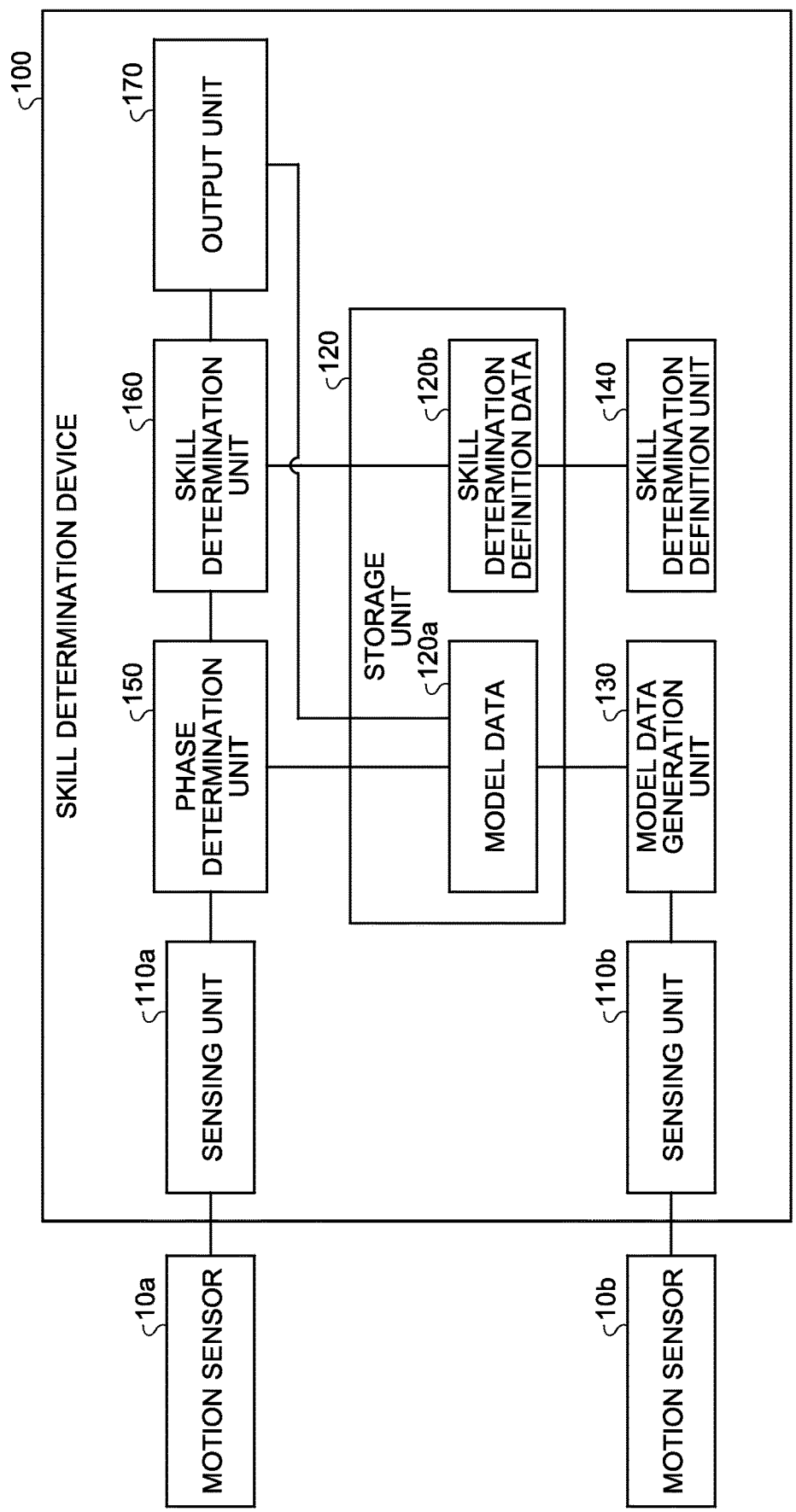
FIG. 1 is a functional block diagram illustrating a configuration of a skill determination device according to a first embodiment.

A configuration of a skill determination device according to a first embodiment will be described. FIG. 1 is a functional block diagram illustrating the configuration of the skill determination device according to the first embodiment. As illustrated in FIG. 1, a skill determination device 100 is connected to motion sensors 10a and 10b. The skill determination device 100 includes sensing units 110a and 110b, a storage unit 120, a model data generation unit 130, a skill determination definition unit 140, a phase determination unit 150, a skill determination unit 160, and an output unit 170.

The motion sensors 10a and 10b will be collectively referred to as a motion sensor 10 if appropriate. The motion sensor 10 is a sensor that detects a motion of a man or an object. For example, the motion sensor 10 detects three-dimensional coordinates of a feature point of a man and outputs sensing information in which the feature point and the three-dimensional coordinates are associated with each other to the skill determination device 100. Here, the feature point of the man corresponds to, for example, the man's head, neck, back, waist or other joint parts.

The motion sensor 10 may output the sensing information using any of the related art. For example, the motion sensor 10 corresponds to a reflective-type MA motion sensor, or a light-receiving type thermal sensor. Alternatively, the sensing information may be extracted by causing the man to wear a three-axis acceleration sensor or a three-axis gyro sensor.

The sensing unit 110a is a processing unit that acquires the sensing information of the user who is coached by an expert from the motion sensor 10. In the following description, the user coached by the expert will be simply referred to as the user. The sensing unit 110a successively acquires the sensing information from the motion sensor 10 as frame data and outputs the information to the phase determination unit 150.

Figure 2:
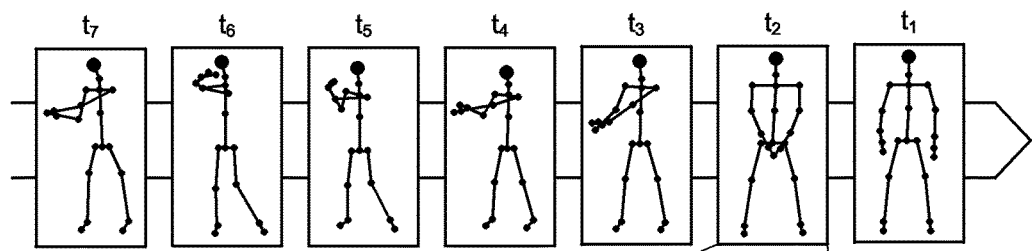
FIG. 2 is a diagram illustrating an example of a data structure of frame data.

FIG. 2 is a diagram illustrating an example of a data structure of the frame data. As illustrated in FIG. 2, the frame data is successively acquired by the sensing unit 110a and output to the phase determination unit 150. Each frame data is associated with each frame number. Although not illustrated, each frame data is associated with time information and output to the phase determination unit 150 in a chronological order. For example, frame data having a frame number "102" represents three-dimensional coordinates of the feature point of the user detected by the motion sensor 10 at a time "$t_2$".

The sensing unit 110b is a processing unit that acquires the sensing information of the expert from the motion sensor 10. The sensing unit 110b successively acquires the sensing information and the frame data from the motion sensor 10 and outputs the information to the model data generation unit 130. A data structure of the frame data of the expert is the same as the data structure of the frame data illustrated in FIG. 2.

Hereinafter, the frame data included in motion data of the expert will be referred to as first frame data for convenience of description. The frame data included in motion data of the user will be referred to as second frame data.

The storage unit 120 has model data 120a and skill determination definition data 120b. The storage unit 120 corresponds to a storage device such as a semiconductor memory device, for example, a random access memory (RAM), a flash memory, and the like and a hard disk drive (HDD).

The model data 120a is information in which the first frame data and types of phases of the first frame data are associated with each other. The model data 120a corresponds to phase definition information. For example, the types of the phases include "start", "backswing", "top", "impact", "follow", "end" and the like. The model data 120a is generated by the model data generation unit 130 to be described later.

FIG. 3 is a diagram illustrating an example of a data structure of the model data. As illustrated in FIG. 3, the model data 120a has metadata 30 and motion data 20. The metadata 30 is information in which a frame number of first frame data and the phase type are associated with each other. The motion data 20 illustrated in FIG. 3 has a plurality of the first frame data.

In the metadata 30 of FIG. 3, an area 30a defines that a type of a frame of second frame data having a frame number "100" is "start". An area 30b defines that a type of a frame of first frame data having a frame number "150" is "backswing". An area 30c defines that a type of a frame of first frame data having a frame number "250" is "top". An area 30d defines that a type of a frame of first frame data having a frame number "450" is "end".

The skill determination definition data 120b is information that defines a feature amount of a motion of the user derived from feature points included in a plurality of second frame data, a determination reference of the skill, and a type of a phase serving as a determination target in an associated manner.

Figure 5:
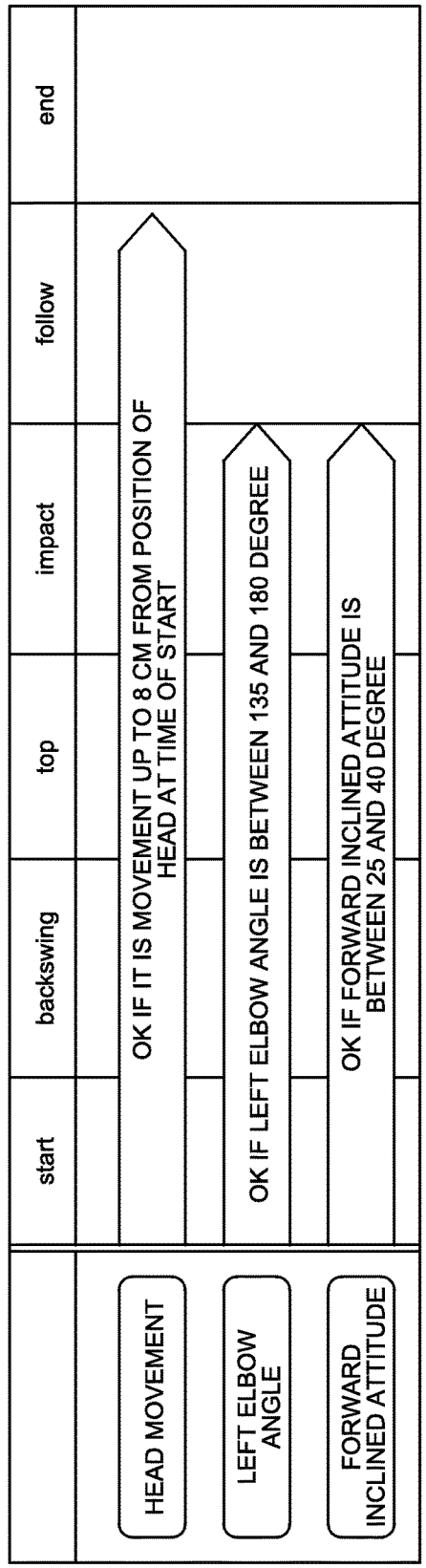
FIG. 5 is a diagram for supplementary description of the skill determination definition data.

FIG. 4 is a diagram illustrating an example of a data structure of the skill determination definition data. FIG. 5 is a diagram for supplementary description of the skill determination definition data. As illustrated in FIG. 4, a module name, a skill determination name, and a parameter definition are associated with each other in the skill determination definition data 120b. The module name is a module name that is used when the skill determination unit 160 to be described later performs determination of a skill. The skill determination name defines a determination name of a skill. The parameter definition has a target phase, a comparative position, and a reference parameter. Here, the skill represents a series of motions, attitudes, and angles of joints while the expert performs swing of a golf or the like, for example. For example, the skill determination name of "head movement" defines the head movement of the expert during the swing as the skill. In addition, the determination reference of the skill uses a series of motions, attitudes, and angles of joints of the expert as a reference and the evaluation is performed depending on a difference between a series of motions, attitudes, and angles of joints of the user and those of the expert through comparison. For example, a set of the target phase, the comparative position, and the reference parameter corresponds to the determination reference of the skill. A process of determining the skill based on this determination reference of the skill will be described later.

The target phase is information which specifies the phase type serving as a skill determination target. The comparative position is information which defines a type of the second frame data to be compared and a position of the feature point. The reference parameter and a reference value are numerical values which are used in the case of determining good or bad of the skill.

A description will be given regarding a record with a module name "PositionChecker" and a skill determination name "head movement" in FIG. 4. The skill determination of "head movement" determines good or bad of the movement of the user's head during swing of a golf driver. Since the target phase is "start-follow", the types of the second phase serving as the determination target are "start, backswing, top, impact, and follow" as illustrated in FIG. 5.

The comparative positions are "start: the head, and current: the head". Thus, a position of a feature point as a comparison source is a position of a feature point of the head of initial second frame data among the second frame data having the phase type of "strat". A position of a feature point as a comparison destination is a position of a feature point of the head of current second frame data.

The reference parameters are "8, 10 and 20". When a difference of a position of the feature point serving as the comparison target is "smaller than 8 cm", the determination result is defined as "Excellent". When the difference of the position of the feature point serving as the comparison target is "8 cm or larger and smaller than 10 cm", the determination result is defined as "Good". When the difference of the position of the feature point serving as the comparison target is "10 cm or larger and smaller than 20 cm", the determination result is defined as "Bad".

Continuously, a description will be given regarding a record with a module name "AngleChecker(1)" and a skill determination name "left elbow angle". The skill determination of "left elbow angle" determines good or bad of an angle of the user's left elbow during the swing of the driver. The target phase is "start-impact". The types of the second phase serving as the determination target are "start, backswing, top, and impact" as illustrated in FIG. 5.

The comparative positions are "current: the left shoulder, current: the left elbow, and current: the left wrist". Thus, an angle formed by a line segment passing through a feature point of the left shoulder of current second frame data and a feature point of the left elbow and a straight line passing through the feature point of the left elbow and a feature point of the left wrist becomes the determination target.

The reference parameters are "(135-180), (130-135, 180-190), and (110-130, 190-200)". When the formed angle is included in "135-180", the determination result is defined as "Excellent". When the formed angle is included in "130-135 and 180-190", the determination result is defined as "Good". When the formed angle is included in "110-130 and 190-200", the determination result is defined as "Bad".

Continuously, a description will be given regarding a record with a module name "AngleChecker(2)" and a skill determination name "forward inclined attitude". The skill determination of "forward inclined attitude" determines good or bad of a forward inclined attitude of the user during the swing of the driver. The target phase is "start-impact". The types of the second phase serving as the determination target are "start, backswing, top, and impact" as illustrated in FIG. 5.

The comparative positions are "current: the head, and current: the waist". Thus, an angle formed by a line segment passing through the feature point of the head of the current second frame data and a feature point of the waist and the perpendicular line becomes the determination target.

The reference parameters are "(25-40), (20-25, 40-55) and (8-20, 55-60)". When the formed angle is included in "25-40", the determination result is defined as "Excellent". When the formed angle is included in "20-25 and 40-55", the determination result is defined as "Good". When the formed angle is included in "8-20 and 55-60", the determination result is defined as "Bad".

The description will be given returning to FIG. 1. The model data generation unit 130 is a processing unit which acquires the motion data of the expert from the sensing unit 110b and generates the model data 120a. The model data generation unit 130 saves the generated model data 120a in the storage unit 120.

For example, the model data generation unit 130 displays the first frame data included in the motion data of the expert on the display device and receives each correspondence of any first frame data with respect to any phase types from an input device. Here, the display device and the input device are not illustrated.

The expert operates the input device and inputs a relationship between the first frame data and the phase type to the model data generation unit 130. The model data generation unit 130 generates the metadata 30 illustrated in FIG. 3 by associating the frame number of the first frame data with the phase type based on the information received from the input device. The model data generation unit 130 saves the metadata 30 and the model data 120*a* having the motion data 20 in the storage unit 120.

The skill determination definition unit 140 is a processing unit that generates the skill determination definition data 120*b*. The skill determination definition unit 140 saves the generated the skill determination definition data 120*b* in the storage unit 120.

For example, the skill determination definition unit 140 displays a setting screen for skill determination definition on the display device and receives the information relating to the skill determination definition from the input device. The expert operates the input device to input the information relating to the skill determination definition. The skill determination definition unit 140 generates the skill determination definition data 120*b* based on the information relating to the skill determination definition and saves the generated data in the storage unit 120.

Figure 6:
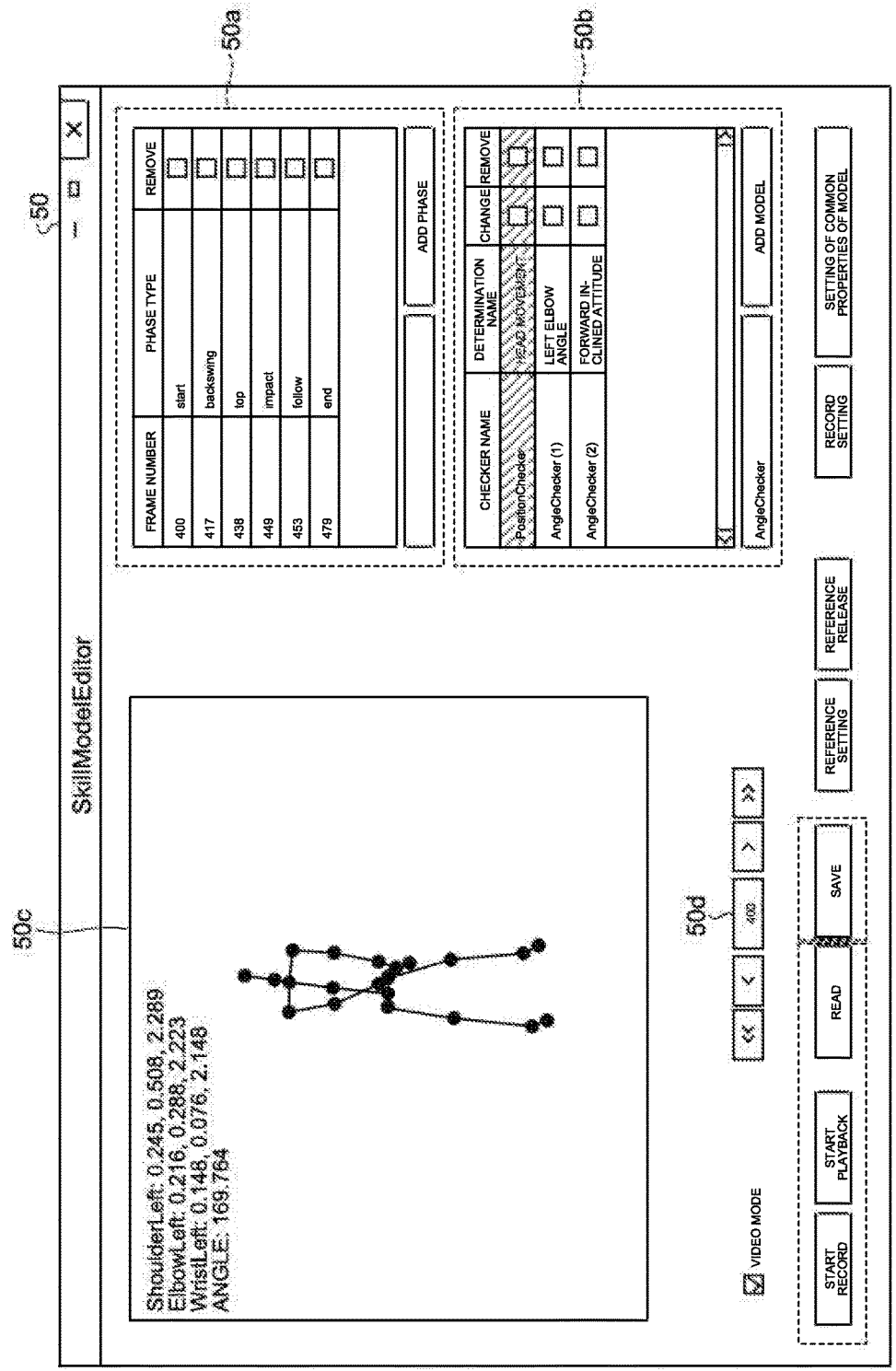
FIG. 6 is a diagram illustrating an example of a display screen which is displayed on a display device.

FIG. 6 is a diagram illustrating an example of a display screen which is displayed on the display device. The display screen 50 includes a phase setting screen 50*a* on which the model data generation unit 130 is displayed and a skill setting screen 50*b* on which the skill determination definition unit 140 is displayed. In addition, a playback screen 50*c* which displays the motion data of the expert and a frame number display screen 50*d* of the current first frame data may be displayed on the display screen 50.

The expert operates the input device to input the correspondence relationship between the frame number and the phase type to the phase setting screen 50*a* while referring to the playback screen 50*c* and the frame number the display screen 50*d*. For example, the model data generation unit 130 generates the model data 120*a* based on the information input to the phase setting screen 50*a*.

The expert operates the input device to select any checker name on the skill setting screen 50*b*. Hereinafter, a description will be given regarding the respective parameter setting screens to be displayed when "PositionChecker", "AngleCheker(1)", and "AngleCheker(2)" are selected.

Figure 7:
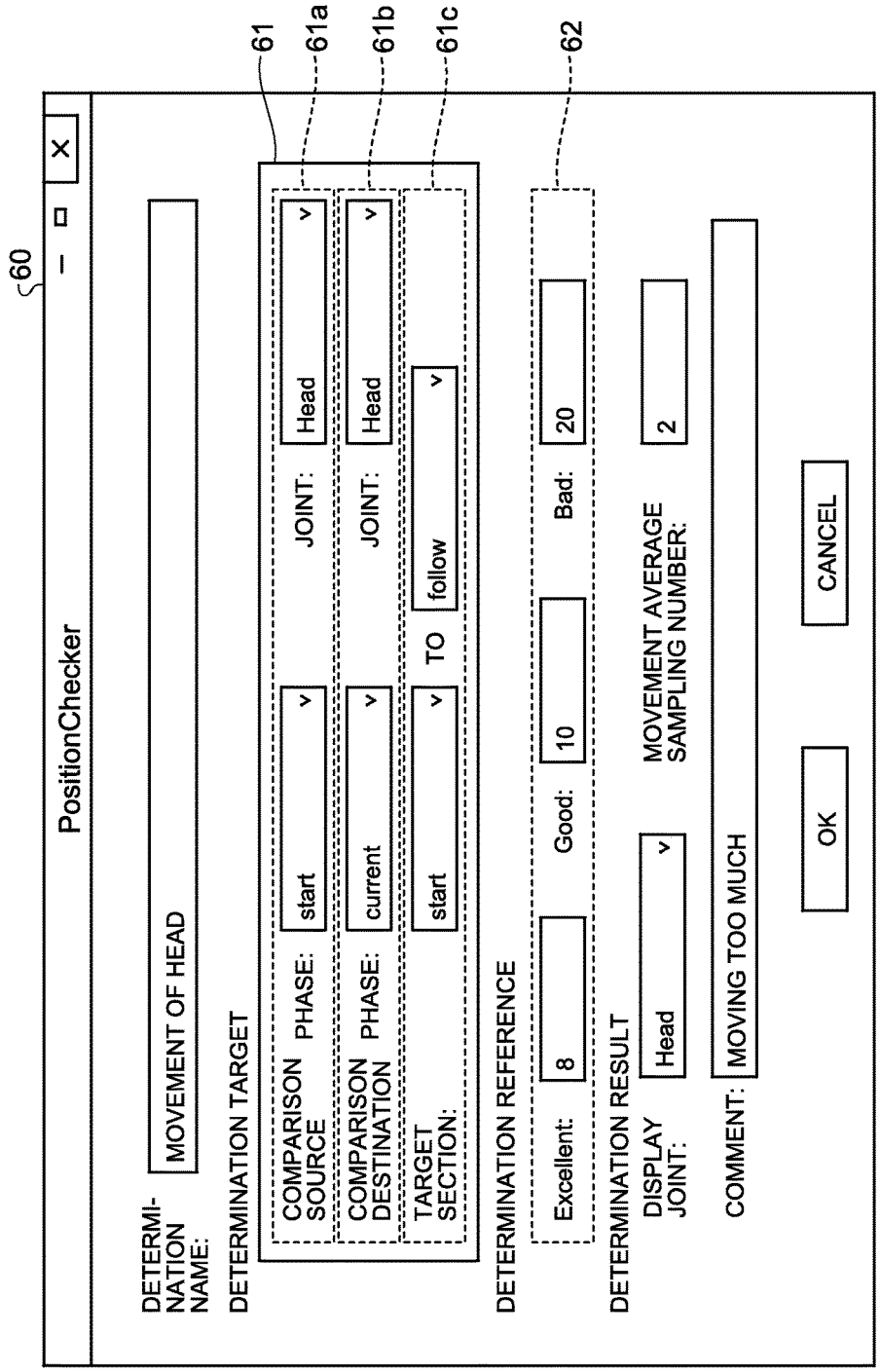
FIG. 7 is a diagram illustrating an example of a parameter setting screen of "PositionChecker".

FIG. 7 is a diagram illustrating an example of the parameter setting screen of "PositionChecker". As illustrated in FIG. 7, a parameter setting screen 60 includes an area 61 to define the determination target and an area 62 to define the determination reference. In addition, the area 61 includes an area 61*a* to define the comparison source, an area 61*b* to define the comparison destination, and an area 61*c* to define a target section. The expert operates the input device to input the information to the respective areas.

In the example illustrated in FIG. 7, it is defined that the position of the feature point as the comparison source is the position of the feature point of the head of the initial second frame data among the second frame data having the phase type of "start" in the area 61*a* to define the comparison source. It is defined that the position of the feature point as the comparison destination is the position of the feature point of the head of the current second frame data in the area 61*b* to define the comparison destination. It is defined that the target phase is "start-follow" in the area 61*c* to define the target section. It is defined that the reference parameters are "8, 10 and 20" in the area 62 to define the determination reference.

For example, the skill determination definition unit 140 generates the record, which corresponds to the module name "PositionChecker" in FIG. 4, based on the information input in FIG. 7.

Figure 8:
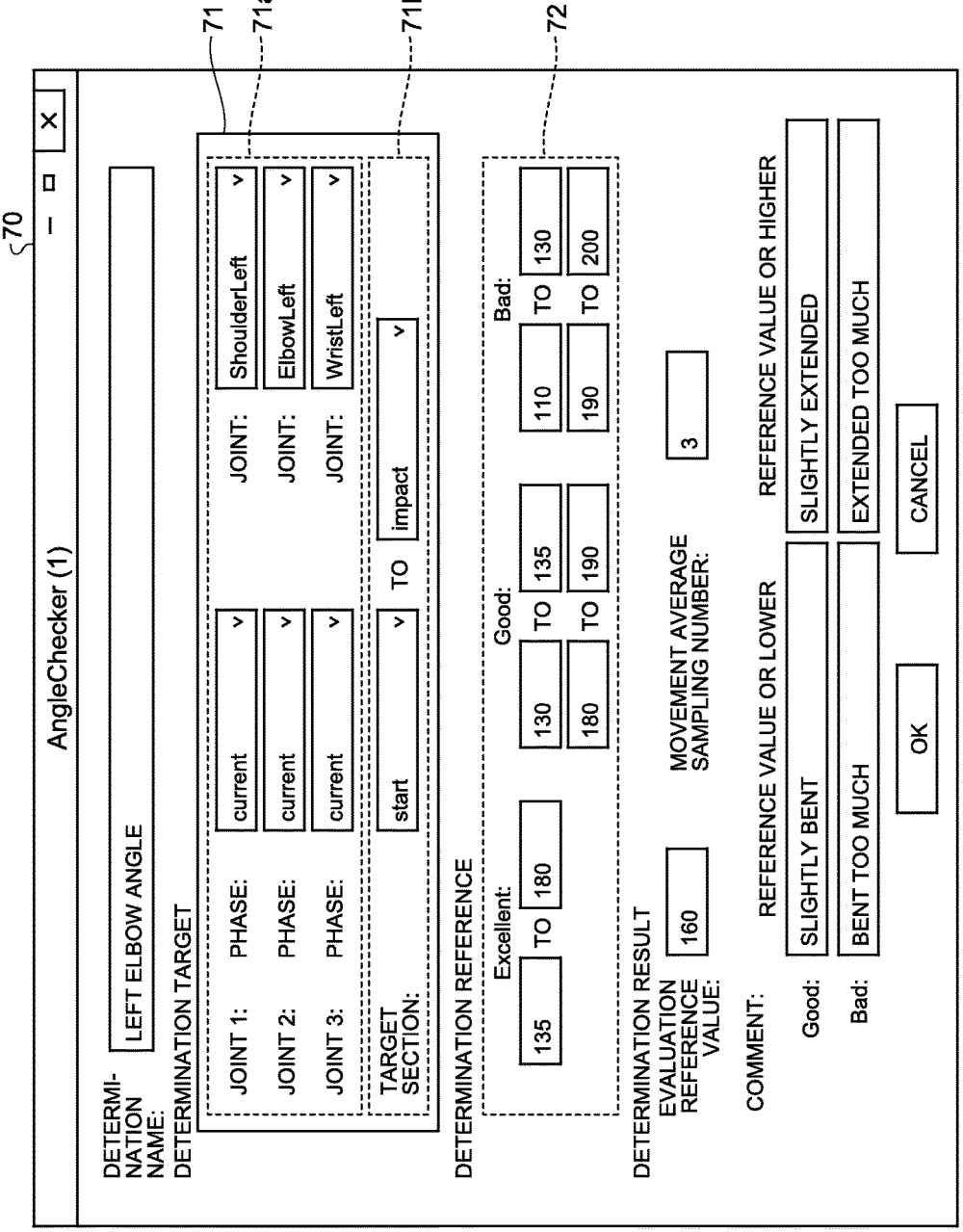
FIG. 8 is a diagram illustrating an example of a parameter setting screen of "AngleChecker(1)".

FIG. 8 is a diagram illustrating an example of the parameter setting screen of "AngleChecker(1)". A parameter setting screen 70 includes an area 71 to define the determination target and an area 72 to define the determination reference. In addition, the area 71 includes an area 71*a* to define the feature point of the comparison target and an area 71*b* to define the target section. The expert operates the input device to input the information to the respective areas.

In the example illustrated in FIG. 8, it is defined that the angle formed by the line segment passing through the feature point of the left shoulder of the current second frame data and the feature point of the left elbow and the straight line passing through the feature point of the left elbow and the feature point of the left wrist is the determination target in the area 71*a* to define the feature point of the comparison target. It is defined that the target phase is "start-impact" in the area 71*b* to define the target section. Various reference parameters are defined in the area 72 to define the determination reference.

For example, the skill determination definition unit 140 generates the record, which corresponds to the module name "AngleChecker(1)" in FIG. 4, based on the information input in FIG. 8.

Figure 9:
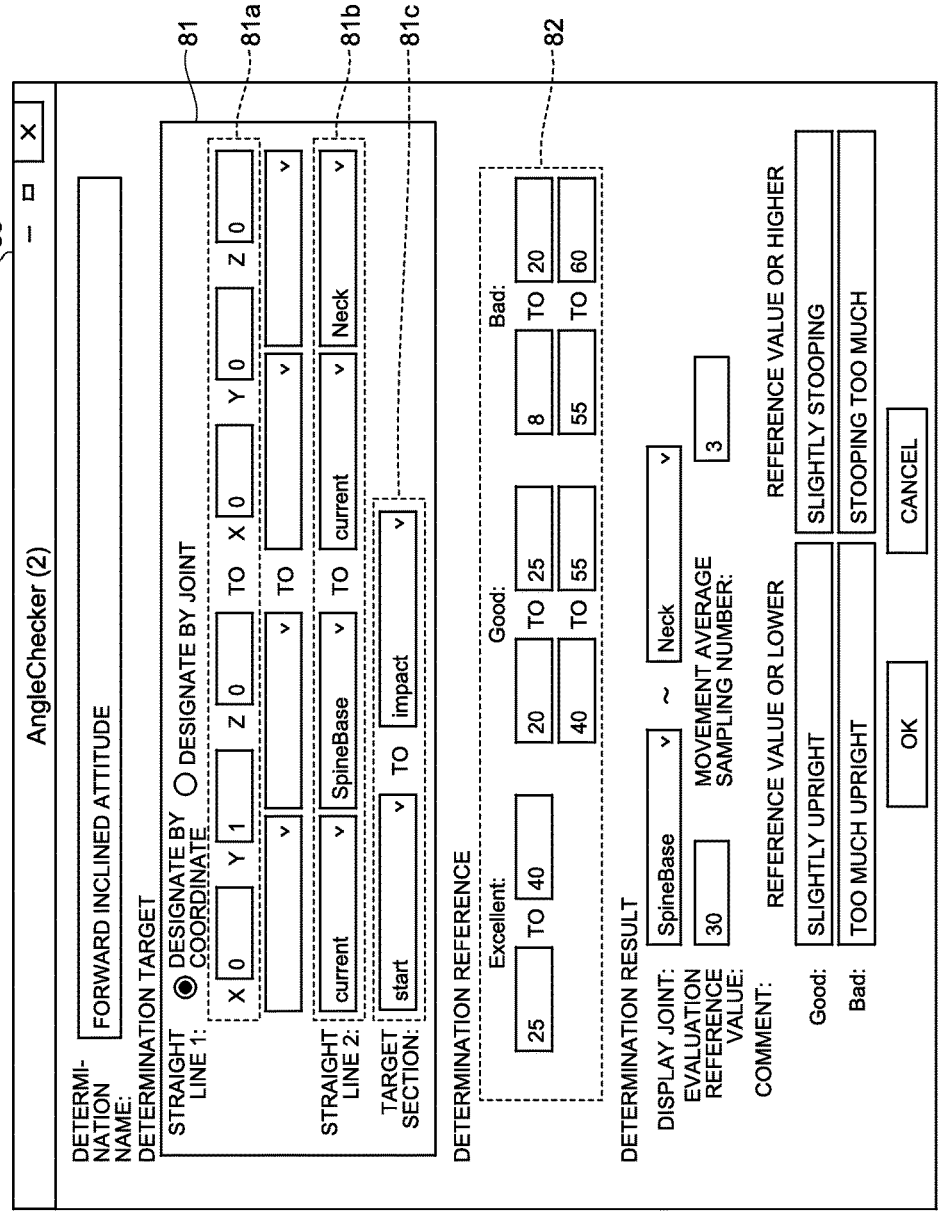
FIG. 9 is a diagram illustrating an example of a parameter setting screen of "AngleChecker(2)".

FIG. 9 is a diagram illustrating an example of the parameter setting screen of "AngleChecker(2)". A parameter setting screen 80 includes an area 81 to define the determination target and an area 82 to define the determination reference. In addition, the area 81 includes an area 81*a* to define the perpendicular line, an area 81*b* to define the feature point of the comparison target, and an area 81*c* to define a target section. The expert operates the input device to input the information to the respective areas.

In the example illustrated in FIG. 9, three-dimensional coordinates of a start point and an end point of the perpendicular line are defined in the area 81*a* to define the perpendicular line. The line segment passing through the feature point of the head of the current second frame data and the feature point of the waist is defined in the area 81*b* to define the feature point of the comparison target. It is defined that the target phase is "start-impact" in the area 81*c* to define the target section. Various reference parameters are defined in the area 82 to define the determination reference.

For example, the skill determination definition unit 140 generates the record, which corresponds to the module name "AngleChecker(2)" in FIG. 4, based on the information input in FIG. 9.

The description will be given returning to FIG. 1. The phase determination unit 150 is a processing unit which determines the phase type corresponding to the second frame data by comparing the respective first frame data included in the model data 120*a* and the second frame data of the user. The phase determination unit 150 grants the determined phase type to the acquired frame data and outputs the data to the skill determination unit 160.

Hereinafter, an example of a process of the phase determination unit 150 will be described in detail. The phase determination unit 150 saves the second frame data of the user in a memory and executes a correction process, feature amount calculation, and frame matching in this order.

A description will be given regarding an example of the correction process which is executed by the phase determination unit 150. The phase determination unit 150 performs vertical axis correction of the second frame data. For example, when the motion sensor 10 is an installation-type sensor, there is a case where an installation position or an installation angle is different from that of the previous environment, and the vertical axis of the second frame data is corrected in accordance with the installation environment. For example, the phase determination unit 150 displays the second frame data on the display device to receive input of correction information from the user and cause the vertical axis of the second frame data to correspond to the perpendicular line. In addition, the phase determination unit 150 may perform correction such that a direction of the user corresponds to a direction facing the front. After receiving the input of the correction information, the phase determination unit 150 may perform the vertical axis correction or the direction correction of the remaining second frame data using the corresponding correction information.

The phase determination unit 150 also executes the correction process for suppressing a variation in the position of the feature point of the second frame data. For example, the phase determination unit 150 suppresses the variation by setting an average value of the positions of the feature points of the previous and subsequent second frame data as the position of the feature point of the second frame data therebetween. In addition, the phase determination unit 150 may remove a noise component included in the second frame data using a low-pass filter.

A description will be given regarding an example of the feature amount calculation which is executed by the phase determination unit 150. In the first embodiment, it is assumed to calculate the three-dimensional coordinates of the feature point with respect to the respective joints included in the second frame data as the feature amount, for example.

A description will be given regarding an example of another feature amount calculation which is executed by the phase determination unit 150. When picking up a joint featuring a unique swing of each of the sports, the phase determination unit 150 may calculate three-dimensional coordinates and speed and acceleration of the hand, the waist, the finger or the like as the feature amount.

When calculating general data, that is not unique in each of the sports as the feature amount, the phase determination unit 150 may calculate three-dimensional coordinates and speed and acceleration of all joints as the feature amount. In addition, the phase determination unit 150 may calculate positions of the center of gravity and the like of all joint positions as the feature amount.

Figure 10:
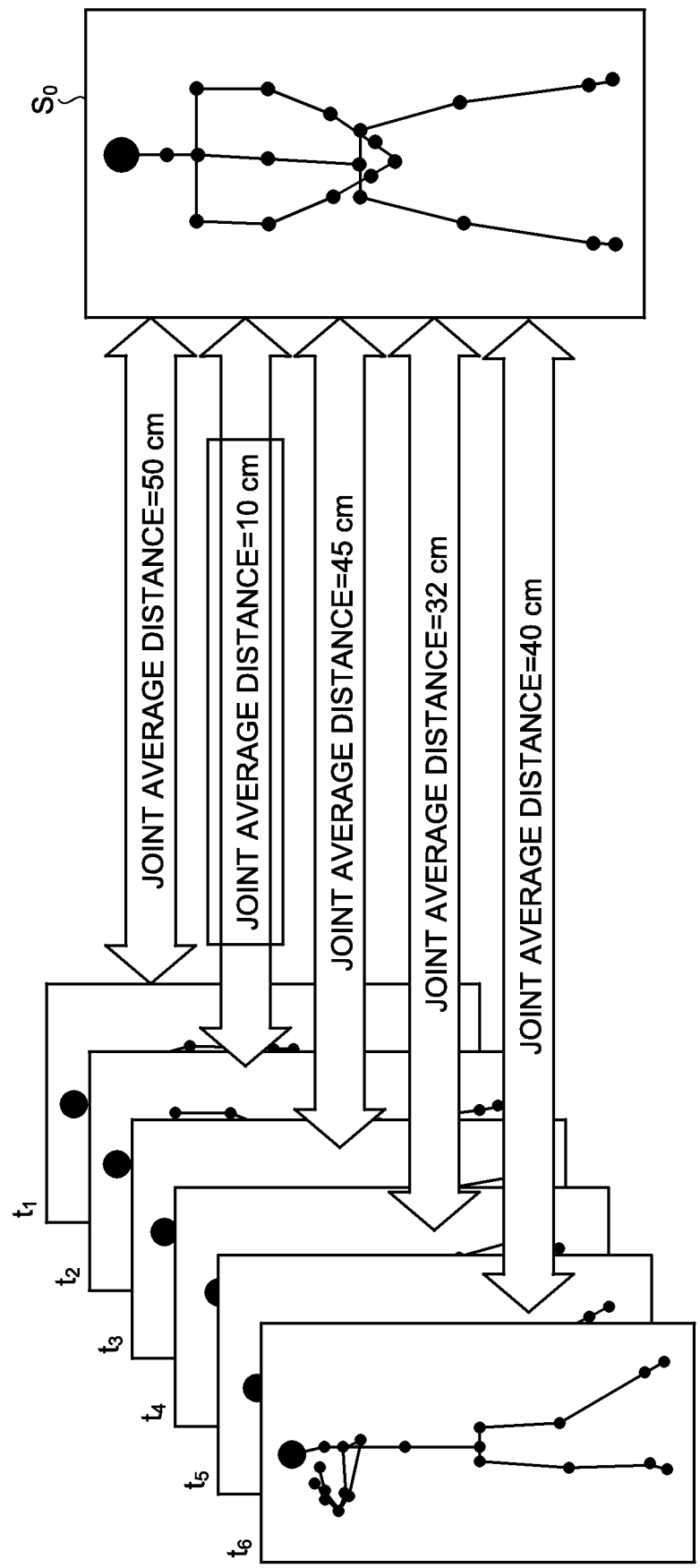
FIG. 10 is a diagram for describing an example of frame matching.

A description will be given regarding an example of the frame matching which is executed by the phase determination unit 150. FIG. 10 is a diagram for describing the example of the frame matching. In the example illustrated in FIG. 10, the current second frame data is set as second frame data $S_0$. In addition, the respective first frame data included in the model data 120a are set as first frame data $t_1$ to $t_6$. The phase determination unit 150 calculates an average value of distances for each of the feature points of the joints based on Formula (1) in regard to the second frame data $S_0$ and the first frame data $t_1$ to $t_6$. In the following description, the average value of distances for each of the feature points of the joints will be referred to as "joint average distance".

$$\underset{i \in R}{\operatorname{argmin}} \left( \sum_{j=1}^{n} \sqrt{(x_{t,j} - x_{S_0 j})^2 + (y_{t,j} - y_{S_0 j})^2 + (z_{t,j} - z_{S_0 j})^2} / n \right) \quad (1)$$

In regard to Formula (1), $x_{S_0 j}$, $y_{S_0 j}$ and $z_{S_0 j}$ are three-dimensional coordinates of a feature point of a certain joint (joint corresponding to a numerical value of j) of the second frame data. Reference signs $x_{tij}$, $y_{tij}$ and $z_{tij}$ are three-dimensional coordinates of a feature point of a certain joint (joint corresponding to the numerical value of j) of first frame data ti. Reference sign n is the number of feature points of the joints. The phase determination unit 150 specifies a set of the second frame data $S_0$ and the first frame data where the joint average distance is the minimum among the respective joint average distances calculated by Formula (1).

In the example illustrated in FIG. 10, the joint average distance in a set of the second frame data $S_0$ and the first frame data $t_2$ is the minimum, and thus, the phase determination unit 150 determines the first frame data corresponding to the second frame data $S_0$ as the first frame data $t_2$. In addition, the phase determination unit 150 determines the phase type of the second frame data $S_0$ as the phase type corresponding to the first frame data $t_2$.

Figure 11:
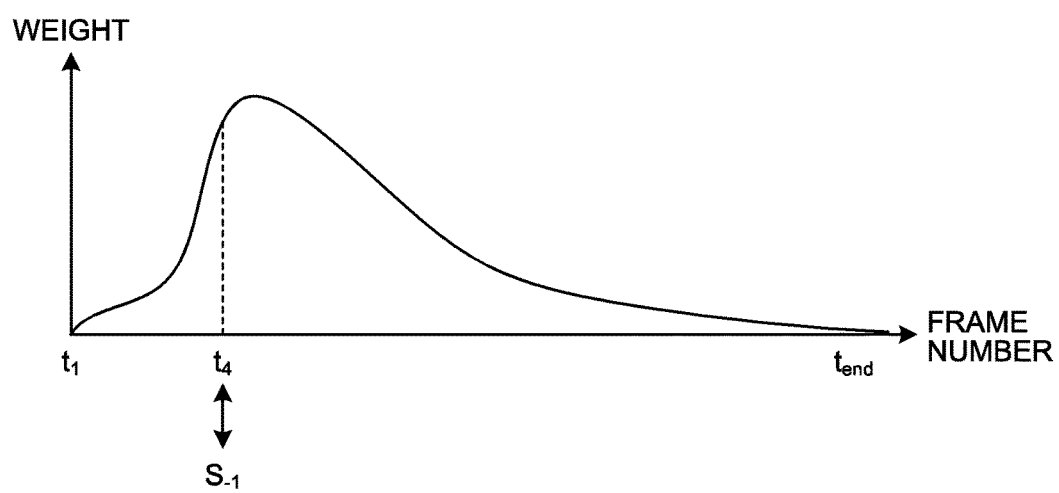
FIG. 11 is a graph for describing a weight.

Meanwhile, the phase determination unit 150 corrects a value of the joint average distance using a weight when calculating the joint average distance using Formula (1). For example, the phase determination unit 150 may correct the joint average distance by dividing the joint average distance by the weight. FIG. 11 is a graph for describing the weight. In FIG. 11, the horizontal axis corresponds to the frame number of the first frame data and the vertical axis corresponds to the weight. For example, the sum of weights corresponding to the respective frame numbers is set as one.

For example, first frame data matched with the second frame data $S_0$ is highly likely to be first frame data that is close to first frame data matched with the previous second frame data $S_{-1}$. For example, when the first frame data matched with the second frame data $S_{-1}$ is set as the first frame data $t_4$, the first frame data matched with the second frame data $S_0$ is highly likely to be the first frame data which is after and close to the first frame data $t_4$.

Thus, the larger weight is set as the first frame data closer to the matched first frame data among the first frame after the first frame data which is matched with the second frame data $S_{-1}$. In addition, the smaller weight is set in the frame before the matched first frame data even if close to the matched first frame data due to the low possibility.

It is possible to prevent the first frame data to be subjected to matching from being out of order or jumping by correcting the value of the joint average distance calculated by Formula (1) using the weight.

The phase determination unit 150 repeatedly executes the above-described process with respect to the other second frame data to determine the first frame data corresponding to each of the second frame data and determine the phase type of each of the second frame data. The phase determination unit 150 extracts the second frame data having the phase types between start and end among the second frame data and saves the extracted data as the motion data in a file and outputs the data to the output unit 170.

The skill determination unit 160 is a processing unit which determines the user's skill for each of the phase types based on the skill determination definition data 120b and the feature amount of the motion, the attitude, and the joint of the user derived from the feature point included in the second frame data which is extracted for each of the phase types.

An example of a process of the skill determination unit 160 will be described. The skill determination unit 160 generates a determination module with reference to the skill determination definition data 120b. For example, the skill determination unit 160 generates the "PositionChecker" module, the "AngleChecker(1)" module, and the "AngleChecker(2)" module in the example illustrated in FIG. 4.

The skill determination unit 160 outputs the second frame data received from the phase determination unit 150 to the corresponding module based on the phase type corresponding to this second frame data and the skill determination definition data 120b. When receiving the second frame data, the module outputs a result of determination of the user's skill based on the data defined in the skill determination definition data 120b.

Figure 12:
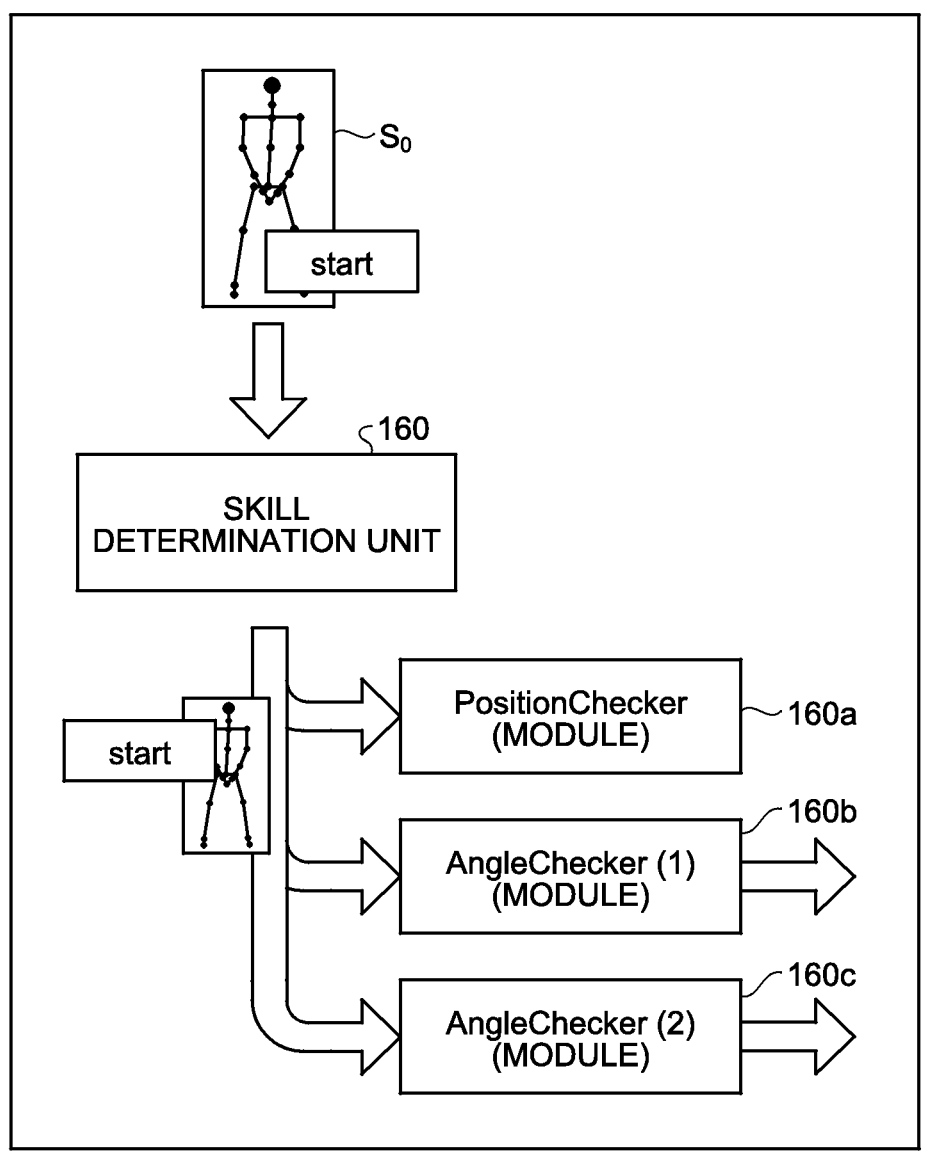
FIG. 12 is a diagram (1) for describing a process of a skill determination unit.
Figure 13:
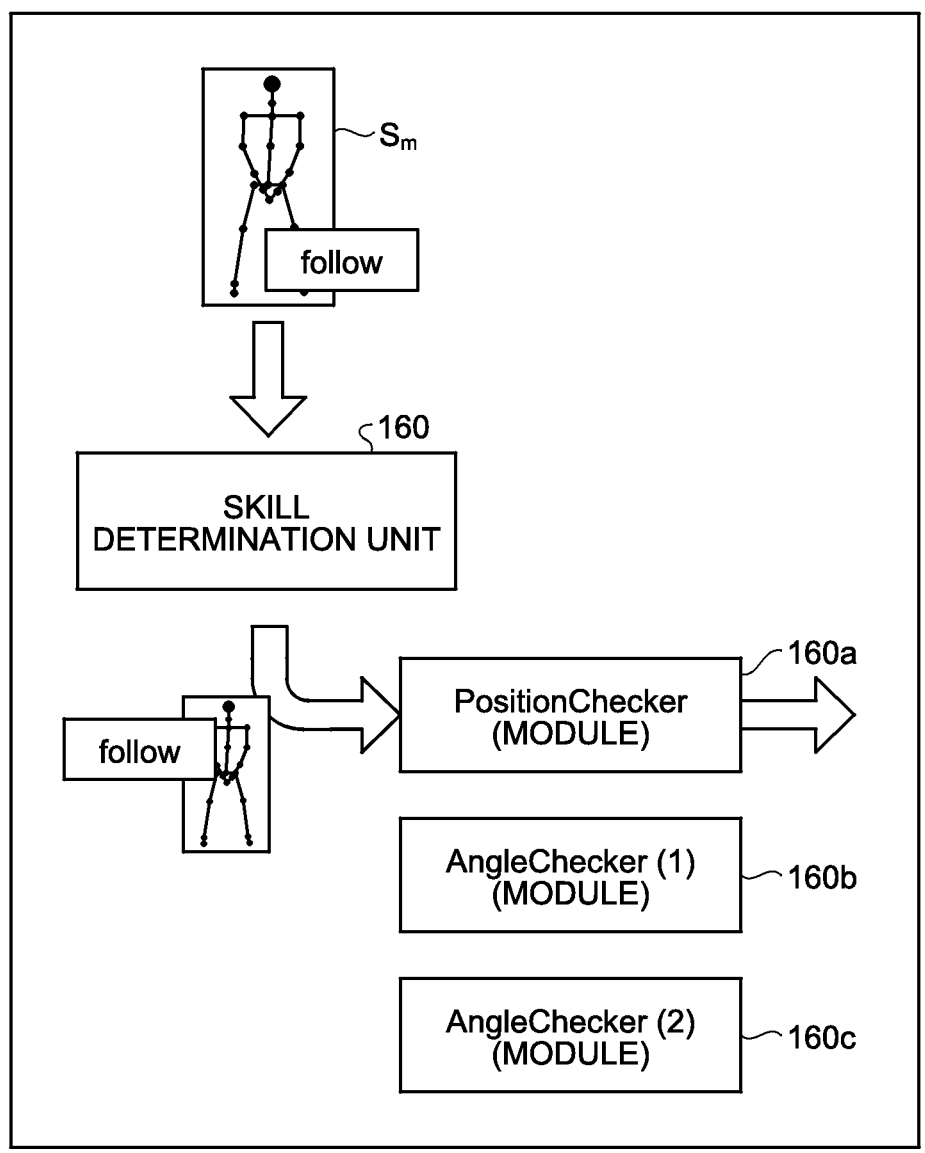
FIG. 13 is a diagram (2) for describing the process of the skill determination unit.

FIGS. 12 and 13 are diagrams for describing the process of the skill determination unit. FIG. 12 will be described. The skill determination unit 160 acquires the second frame data $S_0$ having the phase type "start". As illustrated in FIG. 4, the target phase of "PositionChecker" is "start-follow", and thus, the skill determination unit 160 outputs the second frame data $S_0$ to a "PositionChecker" module 160a. For example, the "PositionChecker" module 160a saves the three-dimensional coordinates of the feature point of the head of the second frame data $S_0$.

As illustrated in FIG. 4, the target phase of "AngleChecker(1)" is "start-impact", and thus, the skill determination unit 160 outputs the second frame data $S_0$ to an "AngleChecker(1)" module 160b. The "AngleChecker(1)" module 160b performs the user's skill determination by evaluating the second frame data $S_0$ based on the comparative position and the reference parameter and outputs the determination result.

For example, when the formed angle is included in "135-180", the "AngleChecker(1)" module 160b outputs the determination result "Excellent". When the formed angle is included in "130-135 and 180-190", the "AngleChecker(1)" module 160b outputs the determination result "Good". When the formed angle is included in "110-130 and 190-200", the "AngleChecker(1)" module 160b outputs the determination result "Bad".

Incidentally, the "AngleChecker(1)" module 160b may output a comment in addition to the determination result. For example, the "AngleChecker(1)" module 160b outputs a comment "slightly bent" when the formed angle is included in "130-135" and outputs a comment "slightly extended" when the formed angle is included in "180-190". The "AngleChecker(1)" module 160b outputs a comment "bent too much" when the formed angle is included in "110-130" and outputs a comment "extended too much" when the formed angle is included in "190-200".

As illustrated in FIG. 4, the target phase of "AngleChecker(2)" is "start-impact", and thus, the skill determination unit 160 outputs the second frame data $S_0$ to an "AngleChecker(2)" module 160c. The "AngleChecker(2)" module 160c performs the user's skill determination by evaluating the second frame data $S_0$ based on the comparative position and the reference parameter and outputs the determination result.

For example, when the formed angle is included in "25-40", the "AngleChecker(2)" module 160c outputs the determination result "Excellent". When the formed angle is "20-25 and 40-55", the "AngleChecker(2)" module 160c outputs the determination result "Good". When the formed angle is "8-20 and 55-60", the "AngleChecker(2)" module 160c outputs the determination result "Bad".

Incidentally, the "AngleChecker(2)" module 160c may output a comment in addition to the determination result. For example, "AngleChecker(2)" the module 160c outputs a comment "slightly upright" when the formed angle is included in "20-25" and outputs a comment "slightly stooping" when the formed angle is included in "40-55". The "AngleChecker(2)" module 160c outputs a comment "too much upright" when the formed angle is included in "8-20" and outputs a comment "stooping too much" when the formed angle is included in "55-60".

Continuously, FIG. 13 will be described. The skill determination unit 160 acquires second frame data $S_m$ having a phase type "follow". As illustrated in FIG. 4, the target phase of "PositionChecker" is "start-follow", and thus, the skill determination unit 160 outputs the second frame data $S_m$ to the "PositionChecker" module 160a.

The "PositionChecker" module 160a performs the user's skill determination by evaluating the second frame data $S_m$ based on the comparative position and the reference parameter and outputs the determination result. For example, the "PositionChecker" module 160a outputs the determination result "Excellent" when a difference between the position of the feature point of the head of the second frame data $S_0$ and the position of the feature point of the head of the second frame data $S_m$ is "smaller than 8 cm". The "PositionChecker" module 160a outputs the determination result "Good" when the difference between the position of the feature point of the head of the second frame data $S_0$ and the position of the feature point of the head of the second frame data $S_m$ is "8 cm or larger and smaller than 10 cm". The "PositionChecker" module 160a outputs the determination result "Bad" when the difference between the position of the feature point of the head of the second frame data $S_0$ and the position of the feature point of the head of the second frame data $S_m$ is "10 cm or larger and smaller than 20 cm".

The "PositionChecker" module 160a may output a comment in addition to the determination result. For example, the "PositionChecker" module 160a outputs a comment "moving too much" when the difference between the position of the feature point of the head of the second frame data $S_0$ and the position of the feature point of the head of the second frame data $S_m$ is "10 cm or larger".

Incidentally, the target phase of "AngleChecker(1)" is "start-impact" as illustrated in FIG. 4, and thus, the skill determination unit 160 does not output the second frame data $S_m$ to the "AngleChecker(1)" module 160b. The target phase of "AngleChecker(2)" is "start-impact", and thus, the skill determination unit 160 does not output the second frame data $S_m$ to the "AngleChecker(2)" module 160c. Incidentally, the skill determination unit 160 may output the second frame data to each of the modules, and each of the modules may individually determine whether to process the second frame data.

The skill determination unit 160 outputs information of the determination result in which the determination results of the respective modules and the second frame data are associated with each other to the output unit 170.

The output unit 170 is a processing unit which outputs the determination result of the skill determination unit 160 through image information, voice information, or physical stimulation with respect to the user. Hereinafter, an example of a process of the output unit 170 will be described.

Figure 14:
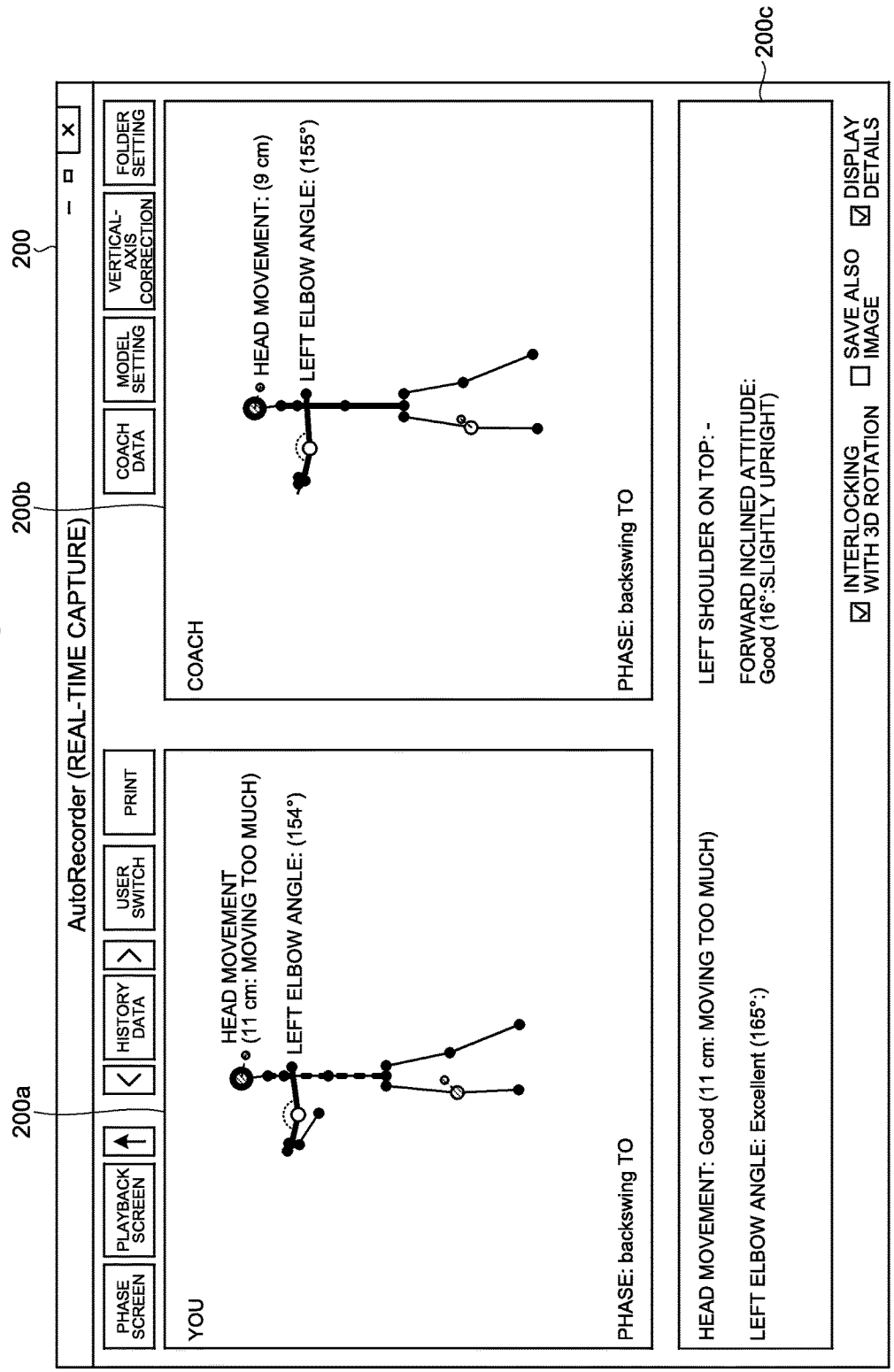
FIG. 14 is a diagram (1) illustrating an example of a display screen which is generated by an output unit.

A description will be given regarding a display screen which is generated by the output unit 170 based on the determination result of the skill determination unit 160. FIG. 14 is a diagram (1) illustrating an example of the display screen which is generated by the output unit. As illustrated in FIG. 14, a display screen 200 includes an own data screen 200a, a model data screen 200b, and a skill determination screen 200c.

The output unit 170 displays the second frame data of the user, acquired from the skill determination unit 160, to the own data screen 200a. In addition, the output unit 170 may perform the display such that the respective feature points of the second frame data, the feature amount of the motion, the attitude, and the joint, and the comment are associated with each other. In the example illustrated in FIG. 14, the output unit 170 displays head movement (11 cm, moving too much) for the head of the feature point. The output unit 170 displays a left elbow angle (154°) for the left shoulder of the feature point.

The output unit 170 displays the first frame data of the model data 120a on the model data screen 200b. For example, the output unit 170 causes the phase type of the first frame data to correspond to the phase type of the second frame data that is being displayed on the own data screen 200a. In addition, the output unit 170 may perform the display such that the respective feature points of the first frame data and the feature amount of the motion, the attitude, and the joint are associated with each other. In the example illustrated in FIG. 14, the output unit 170 displays head movement (9 cm) for the head of the feature point. The output unit 170 displays a left elbow angle (155°) for the left shoulder of the feature point.

The output unit 170 displays the skill determination result, acquired from the skill determination unit 160, to the skill determination screen 200c. For example, the output unit 170 may perform the display such that the skill determination name, the determination result, the feature amount of the motion, the attitude, and the joint, and the comment of are associated with each other.

The output unit 170 may update the display screens 200a, 200b and 200c illustrated in FIG. 14 in real time every time when each of the second frame data is acquired. In addition, the frame data between "start-end" may be played back using the same screen as the screen illustrated in FIG. 14 after determining that the phase type is "End".

In addition, the output unit 170 may change the phases of the second frame data in the own data screen 200a of the display screen 200 in FIG. 14 and perform a process of switching each content of the model data screen 200b and the skill determination screen 200c in accordance with the phase change.

Figure 15:
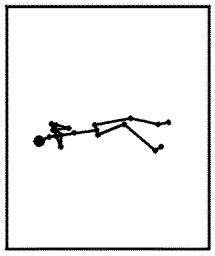
FIG. 15 is a diagram (2) illustrating an example of the display screen which is generated by the output unit.

The output unit 170 may generate a display screen such that the respective phase types, the second frame data, and the determination result are associated with each other. FIG. 15 is a diagram (2) illustrating an example of the display screen which is generated by the output unit. As illustrated in a display screen 210 in FIG. 15, the output unit 170 displays the second frame data of the respective phase types and the determination result in an associated manner. For example, the output unit 170 may perform the display such that the skill determination name, the determination result, the feature amount of the motion, the attitude, and the joint, and the comment of are associated with each other. In addition, the output unit 170 may display the image information in addition with the 3D frame information.

Continuously, a description will be given regarding a process when the output unit 170 outputs the voice information based on the determination result. The output unit 170 may output a skill result or a point that needs to be fixed in the voice in accordance with the determination result output from the skill determination unit 160. For example, the output unit 170 outputs voice, such as "the head moves too much", when the determination result relating to the head movement is Bad. Any voice to be output with respect to any determination result is set in a table or the like in advance, and the output unit 170 outputs the voice based on the corresponding table.

Continuously, a description will be given regarding a process when the output unit notifies the user of the determination result through the physical stimulation. The user wears a device including a small motor, and the output unit 170 causes the small motor to operate in accordance with the determination result. For example, the output unit 170 changes the number of rotations of the small motor in response to the various determination results "Excellent, Good and Bad". The number of rotations of the small motor with respect to the determination result is set in a table or the like in advance, and the output unit 170 causes the small motor to rotate based on the corresponding table.

The user wears a cooling device such as a Peltier element, and the output unit 170 cools the cooling device in accordance with the determination result. For example, the output unit 170 changes the temperature of the cooling device in accordance with the various determination results "Excellent, Good and Bad". The temperature of the cooling device with respect to the determination result is set in a table or the like in advance, and the output unit 170 controls the cooling device based on the corresponding table.

The user wears a device that causes a low-frequency current to flow, and the output unit 170 causes the device to generate the current in accordance with the determination result. For example, the output unit 170 changes the magnitude of the current in accordance with the various determination results "Excellent, Good and Bad". The magnitude of the current with respect to the determination result is set in a table or the like in advance, and the output unit 170 controls the device based on the corresponding table.

Further, the user may wear a power suit or an artificial muscle, and the output unit 170 may cause the power suit or the artificial muscle to move in accordance with the motion data of the expert so that the user may experience the motion of the expert.

Figure 16:
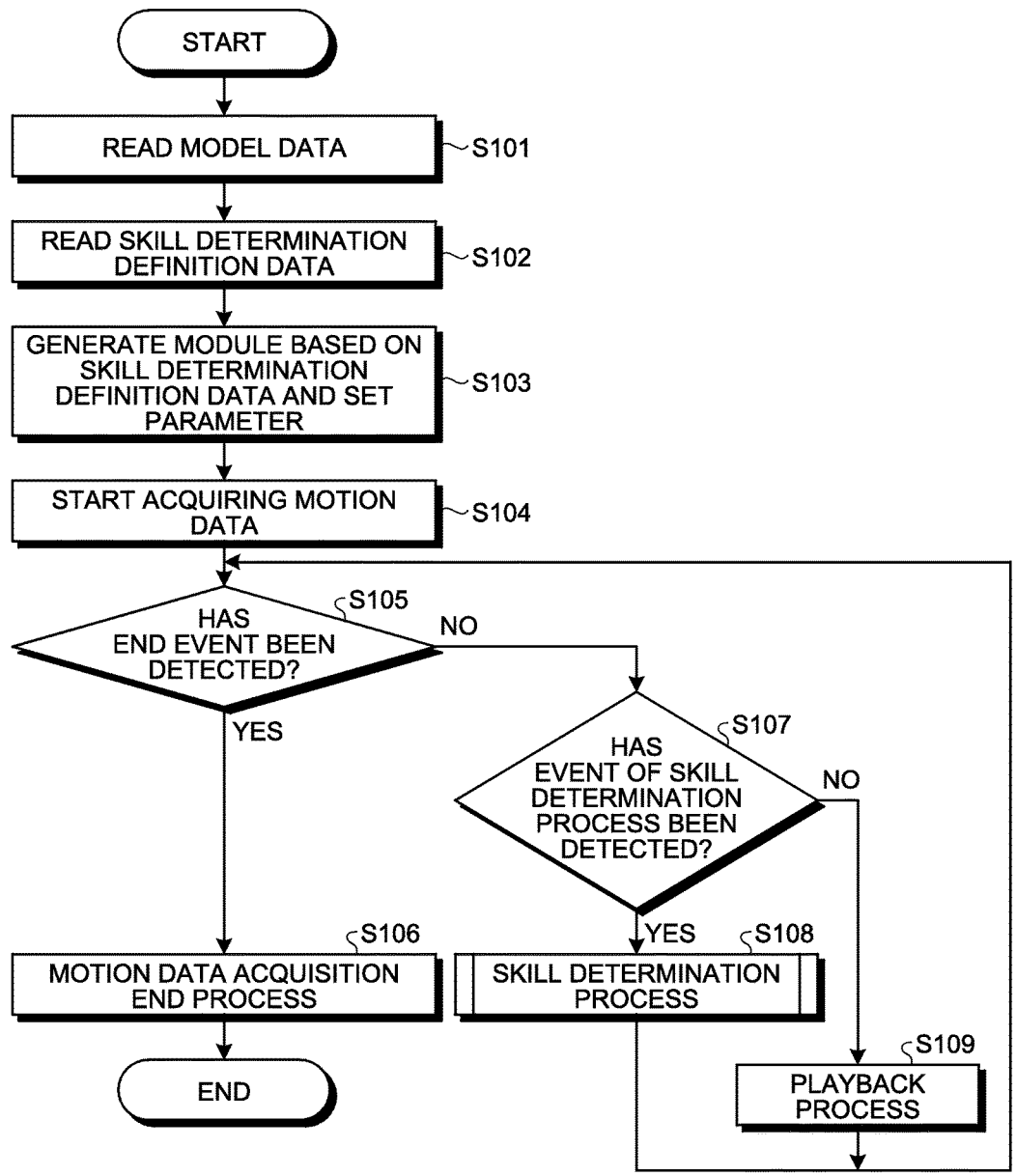
FIG. 16 is a flowchart illustrating a processing procedure of the skill determination device.

Next, a processing procedure of the skill determination device 100 according to the first embodiment will be described. FIG. 16 is a flowchart illustrating the processing procedure of the skill determination device. As illustrated in FIG. 16, the phase determination unit 150 of the skill determination device 100 read the model data 120a (Step S101). The skill determination unit 160 of the skill determination device 100 read the skill determination definition data 120b (Step S102).

The skill determination unit 160 generates the module based on the skill determination definition data 120b and sets a parameter (Step S103). The phase determination unit 150 starts to acquire the motion data of the user (Step S104). The skill determination device 100 determines whether an end event has been detected via the input device (Step S105).

When the skill determination device 100 detects the end event via the input device (Yes in Step S105), the phase determination unit 150 executes a process of ending the acquisition of the user's motion data (Step S106).

On the contrary, the end event has not been detected via the input device (No in Step S105), the skill determination device 100 determines whether an event of the skill determination process has been detected via the input device (Step S107). When the skill determination device 100 has detected the event of the skill determination process via the input device (Yes in Step S107), the skill determination unit 160 executes the skill determination process (Step S108) and transitions to Step S105. Incidentally, the event of the skill determination process is an event that is generated when the sensing unit 110a acquires the frame data from the motion sensor.

On the other hand, when the skill determination device 100 has detected the event of a playback process via the input device (No in Step S107), the output unit 170 of the skill determination device 100 executes the playback process (Step S109) and transitions to Step S105.

Figure 17:
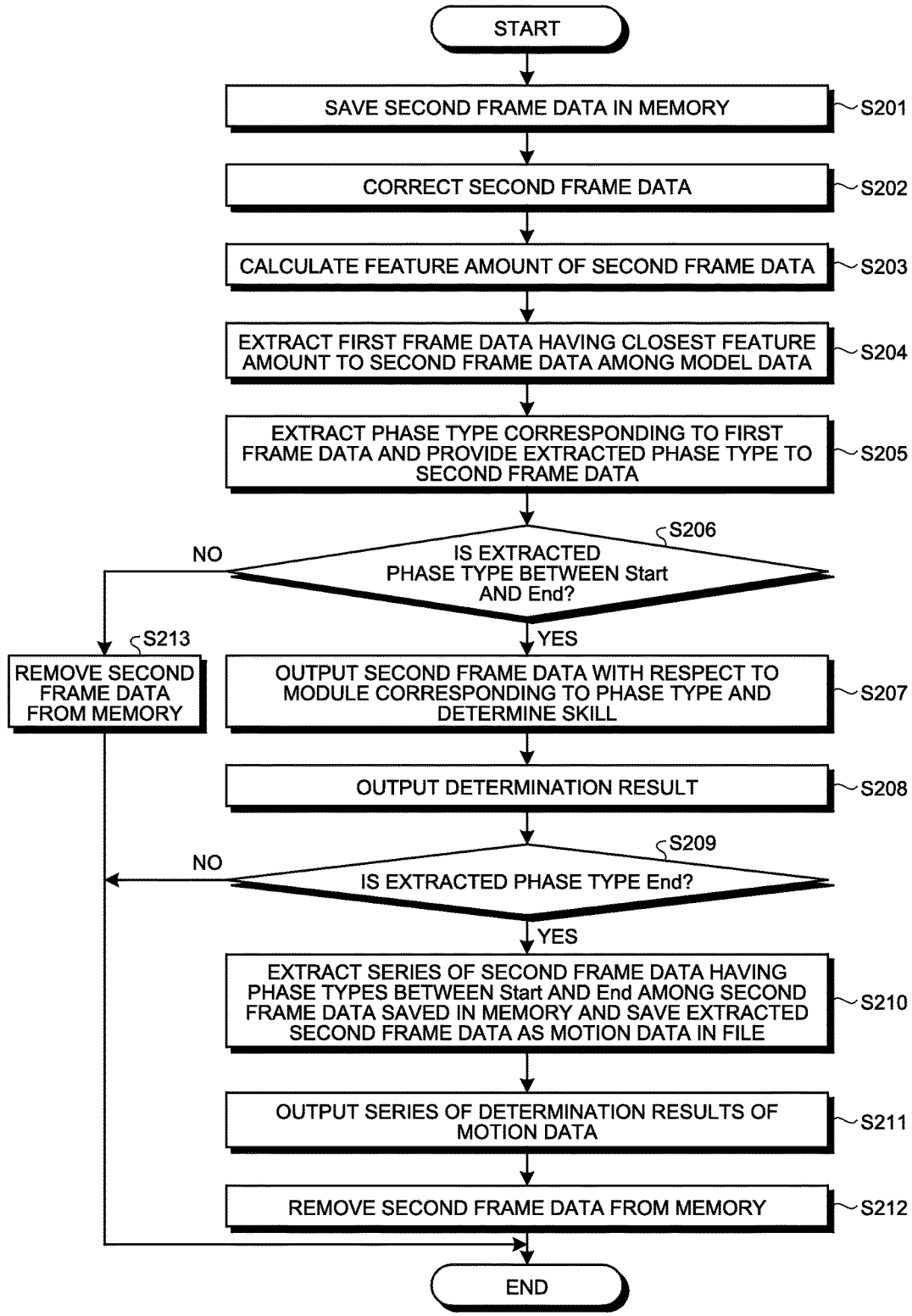
FIG. 17 is a flowchart illustrating a processing procedure of a skill determination process.

Next, the processing procedure of the skill determination process illustrated in Step S108 will be described. FIG. 17 is a flowchart illustrating the processing procedure of the skill determination process. As illustrated in FIG. 17, the phase determination unit 150 of the skill determination device 100 saves the second frame data in the memory (Step S201). The phase determination unit 150 corrects the second frame data (Step S202).

The phase determination unit 150 calculates the feature amount of the second frame data (Step S203). The phase determination unit 150 extracts the first frame data which has the closest feature amount to the second frame data among the model data 120a (Step S204). The phase determination unit 150 extracts the phase type corresponding to the first frame data and grants the extracted phase type to the second frame data (Step S205). Incidentally, the phase types include not only the phase types that have one-to-one correspondence with the frame numbers such as "start" and "backswing" as illustrated in reference sign 50a in FIG. 6 but also the phase types including the phases between "start" and "backswing".

The phase determination unit 150 determines whether the extracted phase type is between "Start" and "End" (Step S206). When the phase type is not between "start" and "End" (No in Step S206), the phase determination unit 150 removes the second frame data stored in S201 from the memory (Step S213) and ends the skill determination process.

On the other hand, when the phase type is between "start" and "End" (Yes in Step S206), the skill determination unit 160 outputs the second frame data to the module corresponding to the phase type and determines the skill (Step S207). The output unit 170 outputs the determination result (Step S208).

The phase determination unit 150 determines whether the extracted phase type is "End" (Step S209). When the extracted phase type is not "End" (No in Step S209), the phase determination unit 150 ends the skill determination process.

On the other hand, when the extracted frame type is "End" (Yes in Step S209), the phase determination unit 150 transitions to Step S210. The phase determination unit 150 extracts a series of the second frame data having the phase types between "Start" and "End" among the second frame data, saved in the memory, and saves the extracted data as the motion data in the file (Step S210). The output unit 170 outputs the determination result of a series of the motion data (Step S211), removes the second frame data stored in S201 from the memory (Step S212), and ends the skill determination process.

Figure 18:
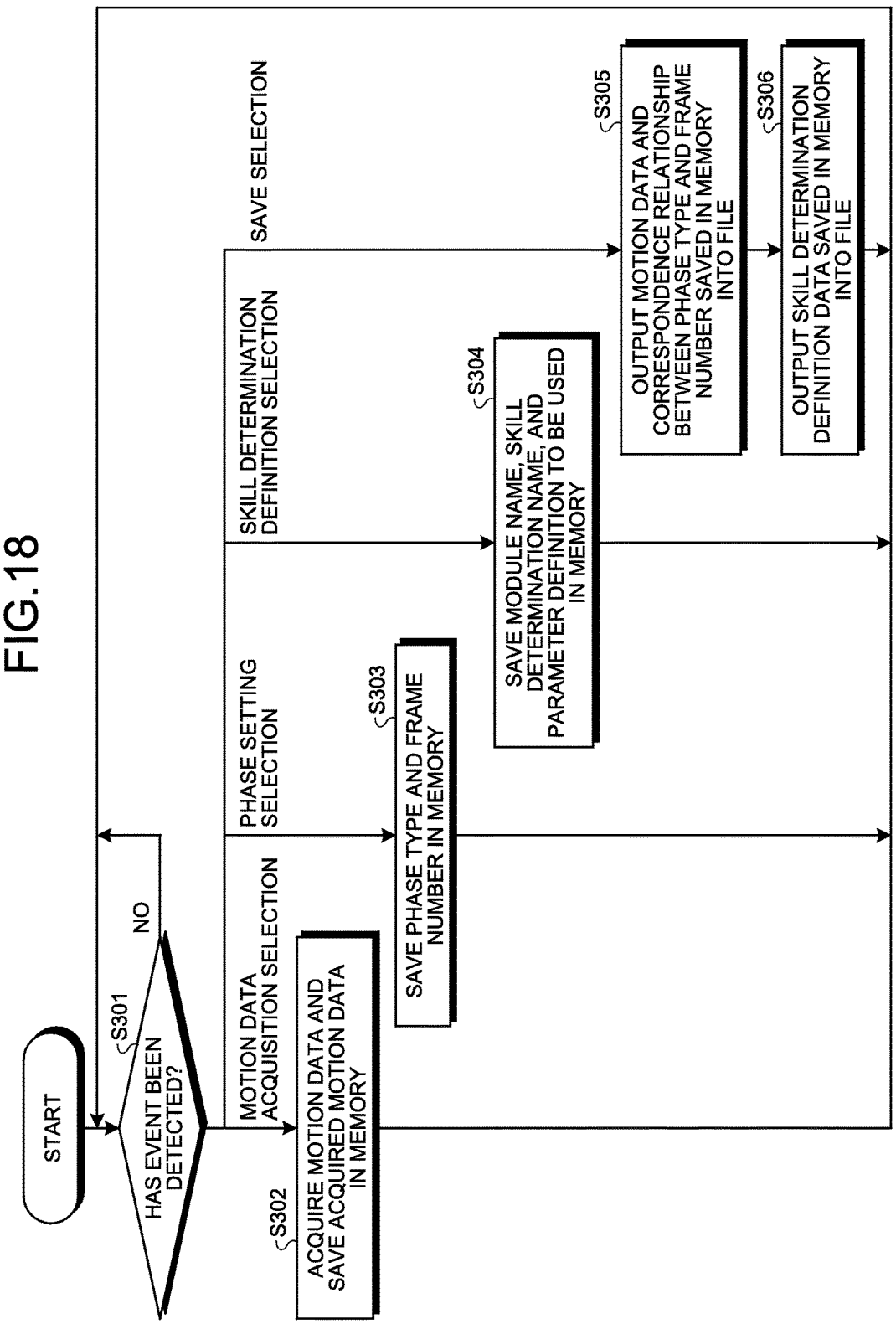
FIG. 18 is a flowchart illustrating a processing procedure of a setting process.

Next, a description will be given regarding a processing procedure of a setting process which is executed by the model data generation unit 130 and the skill determination definition unit 140. FIG. 18 is a flowchart illustrating the processing procedure of the setting process. As illustrated in FIG. 18, the skill determination device 100 determines whether the event has been detected (Step S301). When the event has not been detected (No in Step S301), the skill determination device 100 transitions to Step S301 again.

When an event of motion data acquisition selection has detected (motion data acquisition selection in Step S301), the skill determination device 100 transitions to Step S302. The model data generation unit 130 or the skill determination definition unit 140 acquires the motion data and saves the motion data in the memory (Step S302) and transitions to Step S301.

When an event of phase setting selection has been detected (phase setting selection in Step S301), the skill determination device 100 transitions to Step S303. The model data generation unit 130 saves the phase type and the frame number in the memory (Step S303) and transitions to Step S301.

When an event of skill determination definition selection has been detected (skill determination definition selection in Step S301), the skill determination device 100 transitions to Step S304. The skill determination definition unit 140 saves the module name, the skill determination name, and the parameter definition, which are to be used, in the memory (Step S304) and transitions to Step S301.

When the skill determination device 100 has detected an event of save selection (save selection in Step S301), the model data generation unit 130 outputs the motion data and the correspondence relationship between the phase type and the frame number saved in the memory into the file (Step S305). The skill determination definition unit 140 outputs the skill determination definition data 120b saved in the memory into the file (Step S306) and transitions to Step S301.

Next, an effect of the skill determination device 100 according to the first embodiment will be described. The skill determination device 100 extracts the second frame data corresponding for each of the phase types from the motion data of the user and determines the user's skill with respect to the second frame data for each of the phase types based on the skill determination definition data 120b. Thus, generally, it is possible to automatically determine the user's skill according to the skill determination device 100.

For example, the skill determination definition unit 140 appropriately updates the skill determination definition data 120b to perform the skill determination based on the information from the input device, and the skill determination unit 160 performs the skill determination based on the corresponding skill determination definition data 120b. Since the logic for skill determination is embedded in the related art, a skill determination target is fixed, but the skill determination definition data 120b can be appropriately updated by the skill determination definition unit 140, and accordingly, it is possible to enhance general versatility. In addition, the skill determination definition data 120b is defined as a combination of the module and the parameter definition, and thus, it is easy to reuse the module and the parameter definition which are defined in another target.

In addition, the skill determination device 100 displays the skill determination result associated with the motion data of the user and the motion data of the expert on the display screen. Accordingly, the user can know a point that needs to be improved by himself even if there is no expert around. In addition, it is possible to grasp the point that needs to be improved through the playback after performing swing without caring the screen one by one. In addition, it is possible to compare a difference between the user and the expert and harness the difference for improvement of a skill. In addition, the second frame data of the user is managed in association with the phase type, and thus, can be easily handled in the case of performing the analysis and the like.

The skill determination device 100 determines the phase type corresponding to the second frame data by comparing the model data 120a and the respective second frame data included in the motion data of the user and extracts the second frame data for each of the phase types. For example, the skill determination device 100 specifies the first frame data corresponding to the second frame data using a degree of similarity of each of the first frame data with respect to the second frame data, and determines the phase type corresponding to the first frame data as a type of the second frame data. Thus, it is possible to accurately determine the type of the second frame data of the user and to improve the skill determination accuracy.

When performing the matching, the skill determination device 100 corrects the degree of similarity between the first frame data and the second frame data using the weight. This weight is determined using FIG. 11 based on time of the previously selected first frame data and time of the first frame data serving as a current target of calculation of the degree of similarity. Accordingly, it is possible to prevent the first frame data to be matched with the second frame data from being out of order or jumping.

The skill determination device 100 outputs the skill determination result through the image information, the voice information, or the physical stimulation with respect to the user. Accordingly, it is possible to support improvement of the user's skill using various notification methods.

Meanwhile, the above-described process of the skill determination device 100 is exemplary. Hereinafter, another process which is executed by the skill determination device 100 will be described.

For example, a server on a network may be configured to serve the function of the skill determination device 100. The server acquires and stores the motion data from terminal devices of the user and the expert. In addition, the model data 120a and the skill determination definition data 120b are saved in the server. When being accessed by the user's terminal device, the server displays the motion data and the skill determination result on a web screen of the terminal device.

The skill determination definition unit 140 receives the input from the input device and generates the skill determination definition data 120b, but may automatically generate skill determination definition data 120b based on the model data 120a. For example, the skill determination definition unit 140 analyzes the model data 120a and sets a result obtained from statistical processing of an average value of parameters of the skill determination as the skill determination definition data 120b. For example, an average value of the amount of movement of the feature point of the head of the first frame data included in the model data 120a is set as a. In this case, the skill determination definition unit 140 sets reference parameters of the record having the module name "PositionChecker" as "α, α+a and α+2a". Reference sign a is a numerical value that is appropriately set.

The skill determination unit 160 determines the skill for each of the second frame data and outputs the determination result, but is not limited thereto. The skill determination unit 160 may convert the respective skill determination results into the total score and displays the total score. As illustrated in FIG. 15, for example, the skill determination unit 160 performs the skill determination for each phase, but may convert the determination results between start and end into the total score and display the total score. How much score to be granted to each of the determination results "Excellent, Good and Bad" is set in advance.

The skill determination unit 160 may perform the skill determination process with respect to motion data of the model data as well as the motion data of the user. In this case, the output unit 170 may display a difference between a determination result with respect to the motion data of the model data 120a and the determination result with respect to the motion data of the user.

A way of presenting the motion data output by the output unit 170 is not necessarily fixed. For example, the output unit 170 may receive an operation from the input device and display the motion data at different angles such as a back surface, a side surface and an upper side. In addition, the output unit 170 may change a way of presenting the motion data of the model data 120a interlocking with a change of a way of presenting the motion data of the user.

Meanwhile, the case of performing the skill determination of the golf has been described in the above-described embodiment, but the skill determination device 100 according to the first embodiment can be also applied to the sports other than the golf. For example, the skill determination device 100 can be also applied to tennis, athletics, dance, a way of using cooking equipment, playing of musical instrument, and the like.

Figure 19:
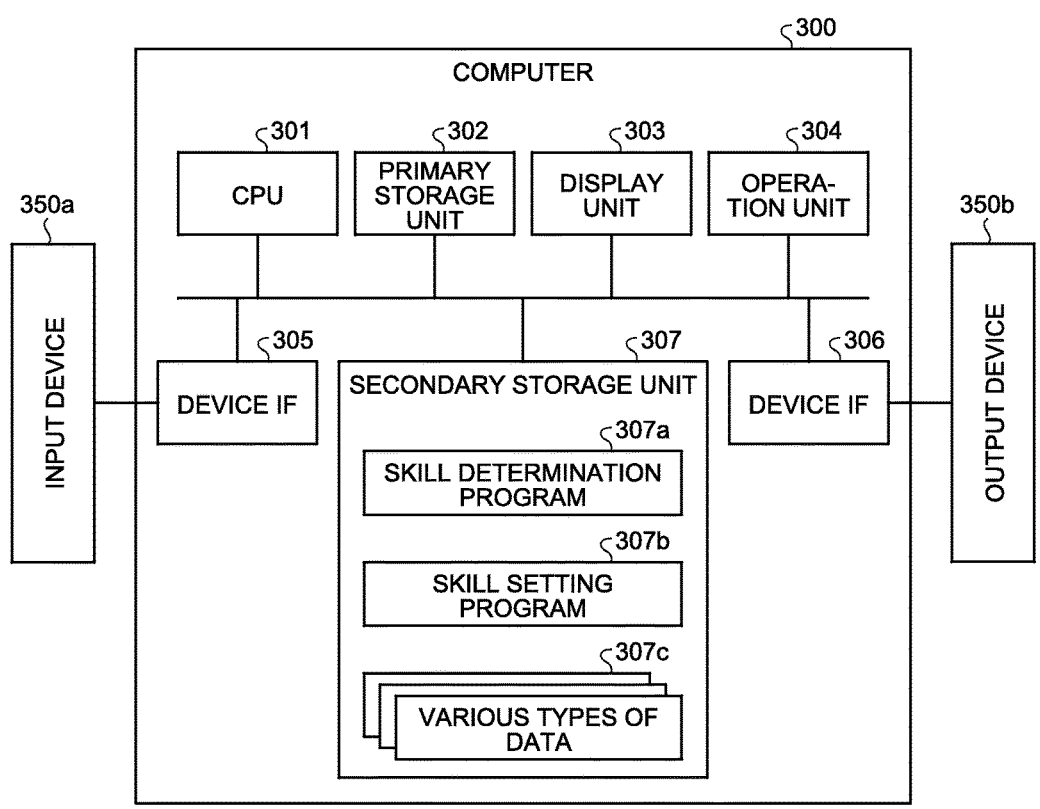
FIG. 19 is a diagram illustrating an example of a computer that executes a skill determination program.

Next, a description will be given regarding an example of a computer that executes a skill determination program which implements the same function as the skill determination device 100 illustrated in the above-described embodiment. FIG. 19 is a diagram illustrating an example of the computer that executes the skill determination program.

As illustrated in FIG. 19, a computer 300 is connected to an input device 350a such as the acceleration sensor and the motion sensor and an output device 350b such as a speaker and a vibrating device. The computer 300 includes a CPU 301 which executes various types of arithmetic processing, a primary storage unit 302 which temporarily stores various types of information, a display unit 303 such as the display, and an operation unit 304 such as the input device. The computer 300 includes a device IF 305 which exchanges data with the input device 350a and a device IF 306 which exchanges data with the output device 350b. In addition, the computer 300 includes a secondary storage unit 307 which corresponds to a hard disk drive.

The secondary storage unit 307 includes a skill determination program 307a, a skill setting program 307b, and various types of data 307c. The skill determination program 307a performs processes corresponding to the phase determination unit 150, the skill determination unit 160, and the output unit 170 of FIG. 1 when being read and executed by the CPU 301. The skill setting program 307b performs processes corresponding to the model data generation unit 130 and the skill determination definition unit 140 of FIG. 1 when being read and executed by the CPU 301. In addition, the various types of data 307c correspond to the model data 120a, the skill determination definition data 120b, the motion data of the user, and the like.

Incidentally, each of the programs 307a and 307b is not necessarily stored in the secondary storage unit 307 from the beginning. For example, the respective programs may be stored in "portable the physical media", such as a flexible disk (FD), a CD-ROM, the DVD disk, a magneto-optical disk, and an IC card, which are inserted into the computer 300. Then, the computer 300 may be configured to read and execute the respective programs 307a and 307b.

Second Embodiment

Figure 20:
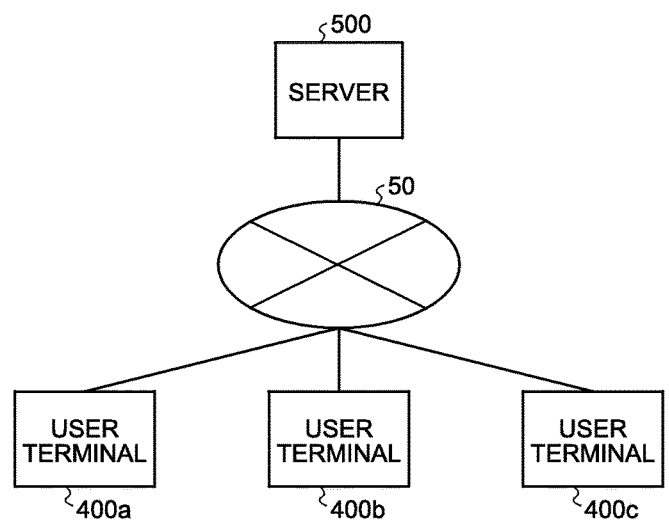
FIG. 20 is a diagram illustrating a configuration of a system according to a second embodiment.

FIG. 20 is a diagram illustrating a configuration of a system according to a second embodiment. As illustrated in FIG. 20, the system includes user terminals 400a, 400b and 400c and a server 500. The user terminals 400a to 400c and the server 500 are connected to each other via a network 50. Although the user terminals 400a to 400c are illustrated as an example, another user terminal may be connected to the network 50. In the following description, the user terminals 400a to 400b will be collectively referred to as a user terminal 400 if appropriate.

The user terminal 400 has the same function as the skill determination device 100 illustrated in the above-described first embodiment. The user terminal 400 is a processing unit which determines user's skill by acquiring the motion data of the user and notifies the server 500 of a result of the skill determination. Incidentally, the user terminal 400 may be connected to the skill determination device 100 and acquire the determination result of the user's skill from the skill determination device 100 as a connection destination.

The user operates the user terminal 400 to access the server 500 and refers to the past skill determination result stored in the server 500.

The server 500 receives information on the skill determination result from the user terminal 400 and holds the information. In addition, when receiving the access with respect to the information on the skill determination result from the user terminal, the server 500 notifies the user terminal 400 of the skill determination result.

Here, the server 500 displays an advertisement banner directly or indirectly relating to a type of sports that has been subjected to the skill determination on a display screen of the user terminal 400 when notifying the user terminal 400 of the information on the skill determination result. In addition, the server 500 displays information on a product on the display screen in accordance with the determination result of the user's skill. For example, the server 500 displays a golf-relating advertisement banner when the type of sports is a golf and notifies the user terminal 400 of information on a golf product for the skill. Incidentally, the user terminal 400 may be similarly notified of the advertisement banner or the information on the product in the case of a baseball, tennis, athletics, dance, a way of using cooking equipment, or playing of musical instrument other than the golf.

Figure 21:
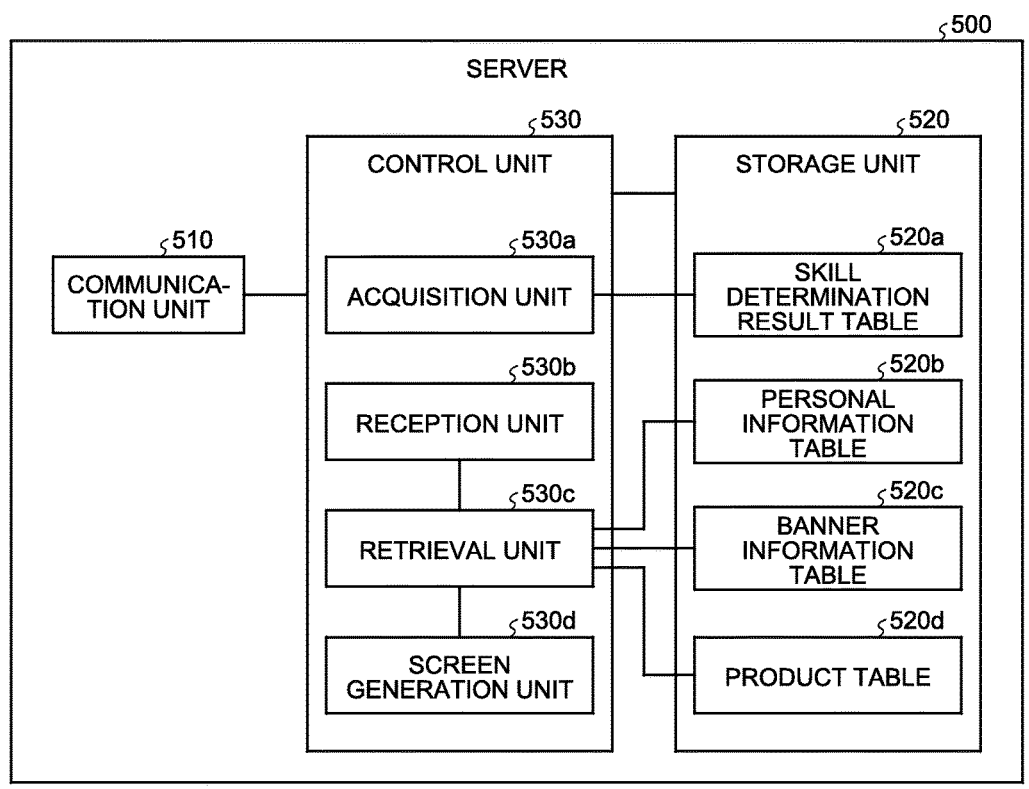
FIG. 21 is a functional block diagram illustrating a configuration of a server according to the second embodiment.

FIG. 21 is a functional block diagram illustrating a configuration of the server according to the second embodiment. As illustrated in FIG. 21, the server 500 includes a communication unit 510, a storage unit 520, and a control unit 530.

The communication unit 510 is a processing unit which executes data communication with the respective user terminals 400 via the network 50. The communication unit 510 corresponds to a communication device. The control unit 530 to be described later exchanges data with the respective user terminals 400 via the communication unit 510.

The storage unit 520 includes a skill determination result table 520a, a personal information table 520b, a banner information table 520c, and a product table 520d. The storage unit 520 corresponds to a storage device such as semiconductor memory device, for example, a random access memory (RAM) and a read only memory (ROM), a flash memory, and the like.

The skill determination result table 520a is a table which holds the information on the skill determination result to be notified by the user terminal 400. FIG. 22 is a diagram illustrating an example of a data structure of the skill determination result table. As illustrated in FIG. 22, user identification information, an item, the skill determination result, and the motion data are associated with each other. The user identification information is information to uniquely identify the user. The item represents an item serving as a target of the skill determination. The skill determination result is a skill determination result with respect to the user who has performed a motion relating to the item.

FIG. 23 is a diagram illustrating examples of the skill determination result. The skill determination results illustrated in FIG. 23 is a skill determination result which corresponds to certain user identification information. For example, each of the skill determination results is associated with a date when the skill determination has been performed. In addition, a determination result of head movement, a determination result of a right elbow angle, a determination result of a forward inclined attitude, and a determination result of waist rotation are associated with each phase in each of the skill determination results. In addition, the skill determination result table 520a may associate the motion data of the user, used as a determination source of the skill determination result, with the skill determination result and hold the resultant although not illustrated here.

The personal information table 520b is a table which holds the user's personal information. FIG. 24 is a diagram illustrating an example of a data structure of the personal information table according to the second embodiment. As illustrated in FIG. 24, the personal information table 520b associates user identification information, an address, a gender, an age, height, and weight with each other. Among them, the user identification information is information to uniquely identify the user. The address is, for example, an electronic mail address (E-mail address) used by the user. The gender, the age, the height, and the weight are a gender, an age, height and weight of the user who is identified by the user identification information.

The banner information table 520c is a table which holds information relating to the advertisement banner to be displayed on the display screen of the user terminal. FIG. 25 is a diagram illustrating an example of a data structure of the banner information table. As illustrated in FIG. 25, the banner information table 520c associates a condition and advertisement banner information with each other. Examples of the condition include the item, the gender and the age. The example illustrated in FIG. 25, for example, illustrates that advertisement banners A1, B1 and C1 are displayed on the display screen of the user terminal 400 when the item corresponding to the skill determination result is "golf", the user's gender is "male and the user's age is "20 years old or older". For example, the advertisement banners A1, B1 and C1 are advertisement banner s which directly or indirectly relates to the item "golf".

The product table 520d is a table which defines a product in accordance with the determination result of the user's skill. FIG. 26 is a diagram illustrating an example of a data structure of the product table. As illustrated in FIG. 26, the product table 520d associates a condition, a product name and comment with each other. The condition represents a condition in the case of selecting a product, and the condition includes an item, the phase, and the determination result. The item is an item that has been subjected to the skill determination. The product name is a name of a product that is recommended to the user. The comment represents a reason of recommending the product or the like. For example, it is defined that a product "golf club A" is recommended when the item is "golf", a determination result of waist rotation is $-45°\pm\alpha$ in the phase "impact", and a determination result of a right knee angle is $10°\pm\alpha$. In addition, it is also defined that a comment "recommend a shaft whose hand side is soft to enable bending to be fully used as a body turn type" is provided when the product "golf club A" is recommended.

The control unit 530 includes an acquisition unit 530a, a reception unit 530b, a retrieval unit 530c, and a screen generation unit 530d. The control unit 530 corresponds to an integrated device, for example, an application specific integrated circuit (ASIC), a field programmable gate array (FPGA), or the like. In addition, the control unit 530 corresponds to an electronic circuit, for example, a CPU, a micro processing unit (MPU), or the like.

The acquisition unit 530a is an acquisition unit which acquires information relating to the skill determination result from the user terminal 400. For example, the information relating to the skill determination result is information in which the user identification information, the item, the skill determination result, and the motion data are associated with each other. The acquisition unit 530a associates the user identification information, the item, and the skill determination result with each other and stores the resultant in the skill determination result table 520a.

When storing the information relating to the skill determination result in the skill determination result table 520a, the acquisition unit 530a adds the information on the skill determination result in a record if the record on the same set of the user identification information and the item has been already stored.

The reception unit 530b is a processing unit which receives access with respect to information on the past skill determination result, which has been stored in the skill determination result table 520a, from the user terminal 400. For example, the user terminal 400 is configured to notify the server 500 of the user identification information when performing the access with respect to the information on the past skill determination result. The reception unit 530b outputs the user identification information received from the user terminal 400 to the retrieval unit 530c.

The retrieval unit 530c is a processing unit which retrieves the past skill determination result corresponding to the user identification information, the advertisement banner information relating to the item serving as the skill determination target, and the product in accordance with the determination result of the user's skill. In the following description, the past skill determination result corresponding to the user identification information will be referred to as history information if appropriate. The retrieval unit 530c outputs the retrieved history information, the advertisement banner information, and the information on the product to the screen generation unit 530d. Hereinafter, an example of a process of the retrieval unit 530c will be described.

First, an example of a process of retrieving the history information in the retrieval unit 530c will be described. The retrieval unit 530c compares the user identification information acquired from the reception unit 530b and the skill determination result table 520a and retrieves the item and the skill determination result corresponding to the user identification information. The retrieval unit 530c outputs the information on the retrieved skill determination result to the screen generation unit 530d as the history information. The item retrieved by the retrieval unit 530c is used in the case of retrieving the advertisement banner information which will be described later. In addition, the information on the skill determination result retrieved by the retrieval unit 530c is used in the case of retrieving the product information which will be described later.

Continuously, an example of a process of retrieving the advertisement banner information in the retrieval unit 530c will be described. The retrieval unit 530c compares the user identification information and the personal information table 520b and specifies the gender and the age corresponding to the user identification information. Then, the retrieval unit 530c compares a set of the item, the gender, and the age with the condition of the banner information table 520c and specifies the corresponding record. The retrieval unit 530c outputs the advertisement banner information included in the specified record to the screen generation unit 530d.

For example, the retrieval unit 530c specifies a record on the first row in FIG. 25 when the set of the item, the gender, and the age is "golf", "male", and "25 years old". Then, the retrieval unit 530c outputs the information of the advertisement banners A1, B1, and C1 to the screen generation unit 530d.

Continuously, an example of a process of retrieving the product information in the retrieval unit 530c will be described. The retrieval unit 530c compares a set of the item and the skill determination result with the condition of the product table 520d and specifies the corresponding record. The retrieval unit 530c outputs the product information included in the specified record to the screen generation unit 530d. Examples of the product information include the product name and the comment. When a plurality of skill determination results are present with respect to the same user identification information, the retrieval unit 530c retrieves the product information using the latest skill determination result.

For example, it is assumed that the item is "golf", and the determination result of waist rotation is "45°±α" and the determination result of the right knee angle is "10°±α" in the phase "impact" included in the skill determination result. In this case, the retrieval unit 530c retrieves a set of the product name and the comment included in a record on the first row of FIG. 26 as the product information.

The screen generation unit 530d is a processing unit which generates a display screen to be displayed on the screen of the user terminal 400. For example, the screen generation unit 530d generates the display screen by arranging the information on the skill determination result, the advertisement banner information, and the product information, which are acquired from the retrieval unit 530c, on the screen. The screen generation unit 530d notifies the user terminal 400, who accessed the skill determination result, of information on the generated display screen.

Next, an example of a processing procedure of the server 500 according to the second embodiment will be described. FIG. 27 is a flowchart illustrating the processing procedure of the server according to the second embodiment. As illustrated in FIG. 27, the reception unit 530b of the server 500 receives the user identification information (Step S301). The retrieval unit 530c of the server 500 retrieves the skill determination result corresponding to the user identification information with reference to the skill determination result table 520a and generates the history information (Step S302).

The retrieval unit 530c retrieves the advertisement banner information with reference to the banner information table 520c (Step S303). The retrieval unit 530c retrieves the product information with reference to the product table 520d (Step S304).

The screen generation unit 530d of the server 500 generates the display screen on which the history information, the advertisement banner information, and the product information are arranged (Step S305). The screen generation unit 530d transmits the information on the display screen to the user terminal 400 (Step S306).

Next, an effect of the server 500 according to the second embodiment will be described. The server 500 displays the advertisement banner directly or indirectly relating to the item that has been subjected to the skill determination on the display screen of the user terminal 400 when notifying the user terminal 400 of the information on the past skill determination result. In addition, the server 500 displays information on a product on the display screen in accordance with the determination result of the user's skill. Accordingly, it is possible to advertise the directly or indirectly relating information to the user who refers to the skill determination result. In addition, it is possible to recommend the product information in accordance with the skill determination result.

Meanwhile, the reception unit 530b of the server 500 may notify the user terminal 400 of billing Information in accordance with the amount of data when the information on the skill determination result from the user terminal 400 is stored in the skill determination result table 520a. For example, the reception unit 530b acquires the amount of data stored in the skill determination result table for each of the user identification information. The reception unit 530b notifies the user terminal 400 corresponding to the user identification information with the amount of data exceeding a threshold that the amount of data to be uploaded exceeds the threshold so that the further upload is subjected to be charged. When the user agrees payment with respect to such notification, the reception unit 530b receives a payment method and saves the method in association with the user identification information.

Incidentally, when notifying the server 500 of the information relating to the skill determination result, the user operating the user terminal 400 may select the data to be notified instead of notifying the server 500 of the entire information relating to the skill determination result. For example, when it is determined that the amount of data relating to the motion data is large, the user can save the amount of data by notifying the server 500 only of the skill determination result. In addition, the user can reduce the amount of data by notifying the server 500 only of a snapshot instead of the motion data.

Third Embodiment

Figure 28:
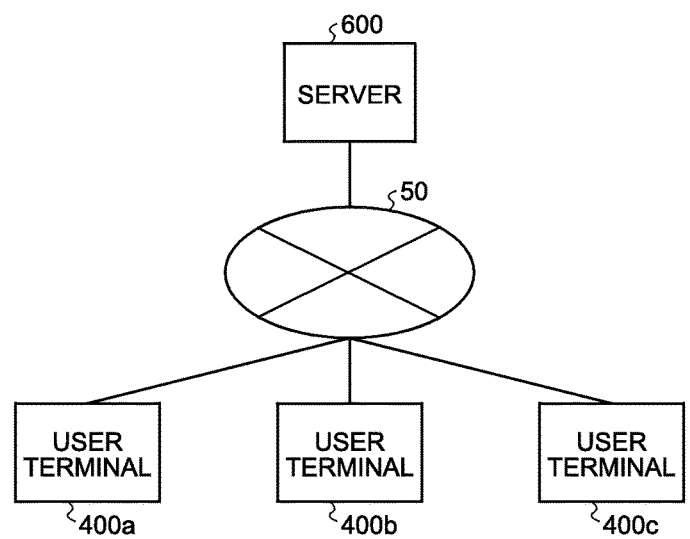
FIG. 28 is a diagram illustrating a configuration of a system according to a third embodiment.

FIG. 28 is a diagram illustrating a configuration of a system according to a third embodiment. As illustrated in FIG. 28, the system includes the user terminals 400a, 400b and 400c and a server 600. The user terminals 400a to 400c and the server 600 are connected to each other via the network 50. Although the user terminals 400a to 400c are illustrated as an example, another user terminal may be connected to the network 50. In the following description, the user terminals 400a to 400c will be collectively referred to as a user terminal 400 if appropriate.

The user terminal 400 has the same function as the skill determination device 100 illustrated in the above-described first embodiment. The user terminal 400 is a processing unit which determines user's skill by acquiring motion data of the user and notifies the server 600 of a result of the skill determination. Incidentally, the user terminal 400 may be connected to the skill determination device 100 and acquire the determination result of the user's skill from the skill determination device 100 as a connection destination.

The server 600 may classify users into a plurality of groups based on features of the users. When receiving the skill determination result from the user terminal 400, the server 600 determines the group to which the user serving as a target of this skill determination belongs and notifies user terminals of the respective users included in the determined group of information on the skill determination result.

Figure 29:
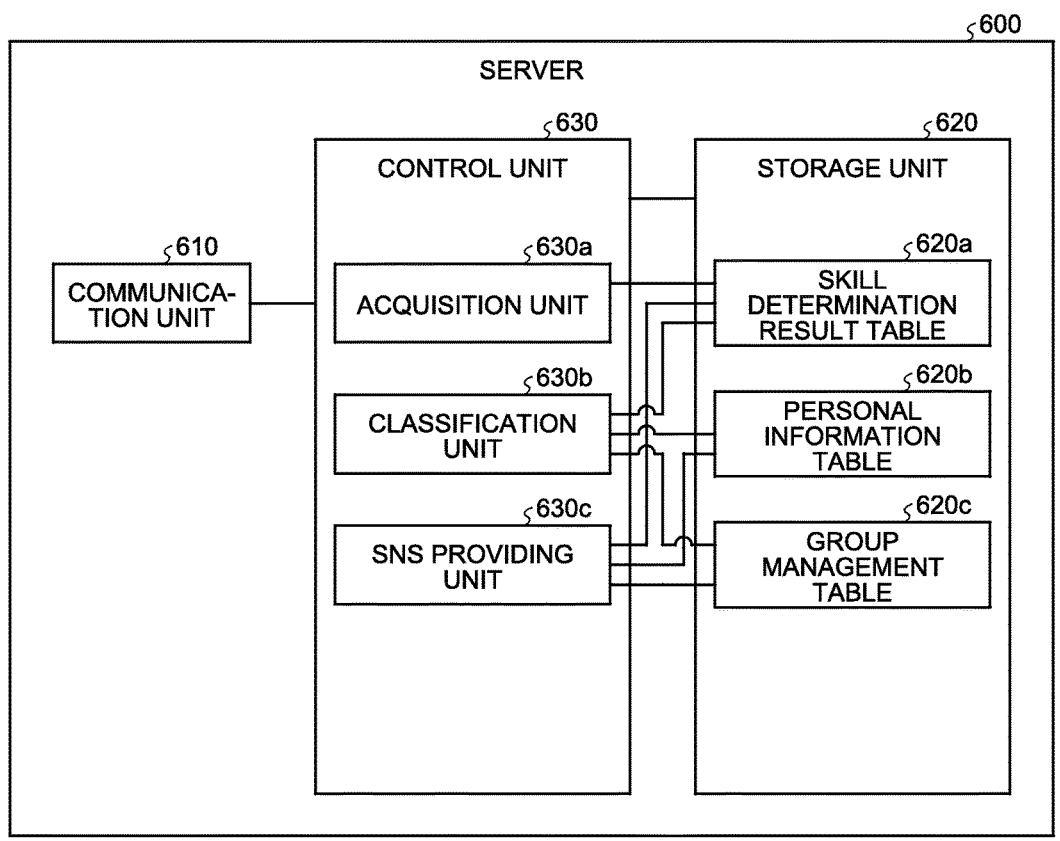
FIG. 29 is a functional block diagram illustrating a configuration of the server according to the third embodiment.

FIG. 29 is a functional block diagram illustrating a configuration of the server according to the third embodiment. As illustrated in FIG. 29, the server 600 includes a communication unit 610, a storage unit 620, and a control unit 630.

The communication unit 610 is a processing unit which executes data communication with the respective user terminals 400 via the network 50. The communication unit 610 corresponds to a communication device. The control unit 630 to be described later exchanges data with the respective user terminals 400 via the communication unit 610.

The storage unit 620 includes a skill determination result table 620a, a personal information table 620b, and a group management table 620c. The storage unit 620 corresponds to a storage device such as a semiconductor memory device, for example, a RAM, a ROM, a flash memory, and the like.

The skill determination result table 620a is a table which holds the skill determination result to be notified by the user terminal 400. A data structure of the skill determination result table 620a is the same as the data structure of the skill determination result table 520a illustrated in FIG. 22, for example.

The personal information table 620b is a table which holds the user's personal information. FIG. 30 is a diagram illustrating an example of a data structure of the personal information table according to the third embodiment. As illustrated in FIG. 30, the personal information table 620b associates user identification information, an address, a gender, an age, height, weight, a school, and a driving range with each other. Among them, the user identification information is information to uniquely identify the user. The address is, for example, an E-mail address used by the user. The gender, the age, the height, and the weight are a gender, an age, height and weight of the user who is identified by the user identification information. The school represents a school of the user. The driving range is a place where the user practices.

The group management table 620c is a table which holds information of the group to which the user belongs. FIG. 31 is a diagram illustrating an example of a data structure of the group management table. As illustrated in FIG. 31, the group management table 620c associates group identification information and affiliated user identification information with each other. The group identification information is information to uniquely identify the group. The affiliated user identification information represents user identification information of users who belong to the group. The example illustrated in FIG. 31, for example, illustrates that users with user identification information "U101, U103, U114, . . . " belong to a group with group identification information "G101".

The control unit 630 includes an acquisition unit 630a, a classification unit 630b, and a social networking service (SNS) providing unit 630c. The SNS providing unit 630c corresponds to a notification unit. The control unit 630 corresponds to an integrated device, for example, an ASIC, a FPGA, and the like. In addition, the control unit 630 corresponds to an electronic circuit, for example, a CPU, an MPU, and the like.

The acquisition unit 630a is an acquisition unit which acquires information relating to the skill determination result from the user terminal 400. For example, the information relating to the skill determination result is information in which user identification information, an item, and the skill determination result are associated with each other. The acquisition unit 630a associates the user identification information, the item, and the skill determination result with each other and stores the resultant in the skill determination result table 620a.

When storing the information relating to the skill determination result in the skill determination result table 620a, the acquisition unit 630a adds the information on the skill determination result in a record if the record on the same set of the user identification information and the item has been already stored.

The classification unit 630b is a processing unit which classifies the user identification information into groups for each of features of users with reference to the personal information table 620b. The classification unit 630b associates the group identification information and the user identification information which belongs to the group of the group identification information with each other based on a classified result and registers the resultant in the group management table 620c.

Hereinafter, an example of a process of the classification unit 630b will be described. For example, the classification unit 630b specifies the user identification information belong to the same school with reference to the personal information table 620b and classifies the specified user identification information into the same group. Alternatively, the classification unit 630b specifies the user identification information belong to the same driving range with reference to the personal information table 620b and classifies the specified user identification information into the same group.

The above-described classification process is exemplary, and the classification unit 630b may classify the user identification information into a group of the same age, a group of family, and a group that is coached by the same coach. In addition, the classification unit 630b may classify the user identification information with the same skill level into the same group with reference to the skill determination result table 620a. For example, the classification unit 630b may obtain scores of the respective user identification information by summing scores in accordance with good, bad and excellent included in the skill determination results and classify the user identification information having the similar scores into the same group.

The SNS providing unit 630c is a processing unit which provides the SNS to the respective user terminals 400. For example, the SNS providing unit 630c cause the information on the skill determination result or information on another electronic bulletin board to be shared among users of the user identification information that belong to the same group with reference to the group management table 620c.

For example, the SNS providing unit 630c determines the user identification information that belongs to the same group as the user identification information corresponding to the skill determination result based on the group management table 620c when the information on the skill determination result is registered in the skill determination result table 620a. The SNS providing unit 630c notifies the user terminal 400 corresponding to the specified user identification information of the information on the skill determination result registered in the skill determination result table 620a. The SNS providing unit 630c may specify the address of the user identification information which belongs to the group with reference to the personal information table 620b and notify the information on the skill determination result using the address as a destination.

For example, the user identification information U101, U103 and U114 belong to the group having the group identification information "G101" with reference to FIG. 31. In addition, it is assumed that the skill determination result of the user identification information U101 is registered in the skill determination result table 620a by the acquisition unit 630a. In this case, the SNS providing unit 630c notifies the user terminal 400 of the user identification information U103 and U114 in the same group of the skill determination result of the user identification information U101.

Figure 32:
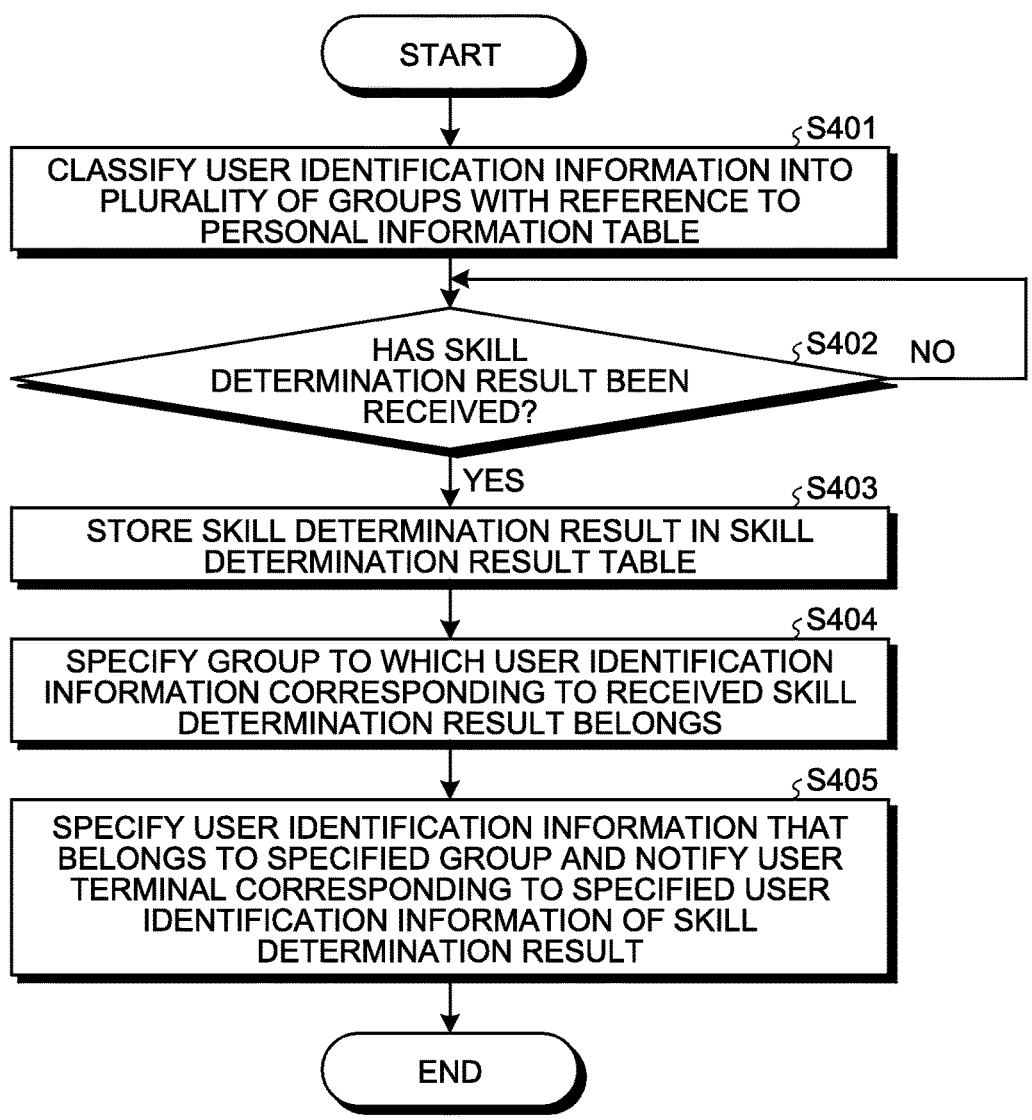
FIG. 32 is a flowchart illustrating a processing procedure of the server according to the third embodiment.

Next, an example of a processing procedure of the server 600 according to the third embodiment will be described. FIG. 32 is a flowchart illustrating the processing procedure of the server according to the third embodiment. As illustrated in FIG. 32, the classification unit 630b of the server 600 classifies the user identification information into the plurality of groups with reference to the personal information table 620b (Step S401).

The SNS providing unit 630c of the server 600 determines whether the skill determination result has been received (Step S402). When the skill determination result has not been received (No in Step S402), the SNS providing unit 630c transitions to Step S402 again.

When the skill determination result has been received (Yes in Step S402), the SNS providing unit 630c stores the received skill determination result in the skill determination result table 620a (Step S403). The SNS providing unit 630c specifies the group to which the user identification information corresponding to the received skill determination result belongs (Step S404).

The SNS providing unit 630c specifies the user identification information that belongs to the specified group and notifies the user terminal 400 corresponding to the specified user identification information of the skill determination result (Step S405).

Next, an effect of the server 600 according to the third embodiment will be described. The server 600 classifies the user identification information into the plurality of groups based on features of the users. When receiving the skill determination result from the user terminal 400, the server 600 determines the group to which the user serving as the skill determination target belongs and notifies the user terminals of the respective user identification information included in the determined group of the information on the skill determination result. Thus, it is possible to make communication among the respective users who belong to the same group easy. For example, it is possible to exchange an advice for improvement of the skill on the social network. In addition, the above-described process can be used as a site or an off-line window indirectly relating to solicitation to the item, solicitation to an event, or solicitation to a meeting.

Fourth Embodiment

Figure 33:
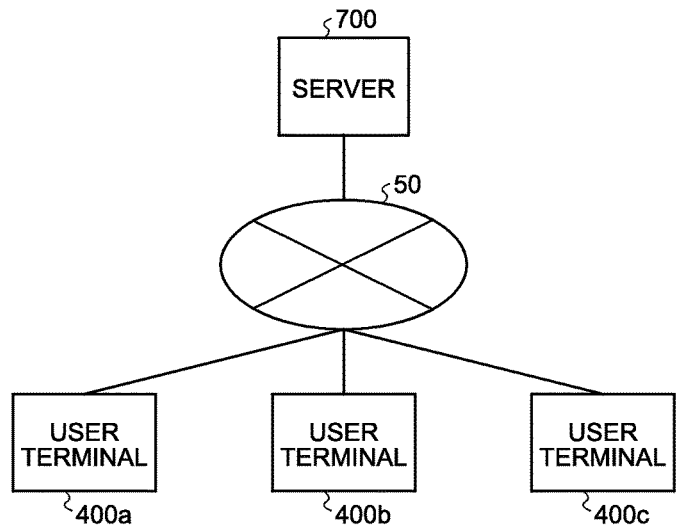
FIG. 33 is a diagram illustrating a configuration of a system according to a fourth embodiment.

FIG. 33 is a diagram illustrating a configuration of a system according to a fourth embodiment. As illustrated in FIG. 33, the system includes the user terminals 400a, 400b and 400c and a server 700. The user terminals 400a to 400c and the server 700 are connected to each other via the network 50. Although the user terminals 400a to 400c are illustrated as an example, another user terminal may be connected to the network 50. In the following description, the user terminals 400a to 400b will be collectively referred to as a user terminal 400 if appropriate.

The user terminal 400 has the same function as the skill determination device 100 illustrated in the above-described first embodiment. The user terminal 400 is a processing unit which determines user's skill by acquiring motion data of the user and notifies the server 700 of a result of the skill determination. Incidentally, the user terminal 400 may be connected to the skill determination device 100 and acquire the determination result of the user's skill from the skill determination device 100 as a connection destination.

In addition, the user operates the user terminal 400 to acquire model data of his favorite expert from the server 700 and determines the user's skill using the acquired model data of the expert.

The server 700 is a server which manages a plurality of types of the expert model data. When being accessed by the user terminal 400, the server 700 displays the plurality of types of the expert model data and receives selection of any expert model data. When receiving the selection of the expert model data, the server 700 notifies the user terminal 400 of the model data for which the selection has been received. Incidentally, the server 700 may select the expert model data suitable for the user and notify the user terminal 400 of the selected expert model data.

Figure 34:
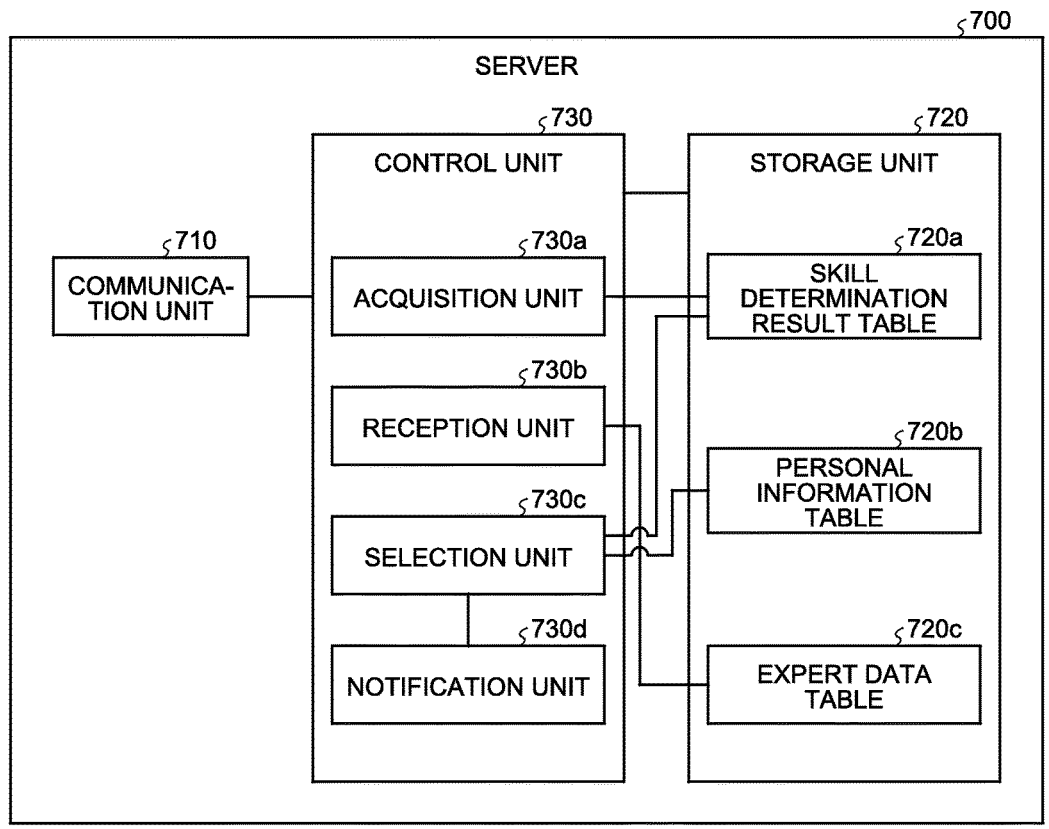
FIG. 34 is a functional block diagram illustrating a configuration of the server according to the fourth embodiment.

FIG. 34 is a functional block diagram illustrating a configuration of the server according to the fourth embodiment. As illustrated in FIG. 34, the server 700 includes a communication unit 710, a storage unit 720, and a control unit 730.

The communication unit 710 is a processing unit which executes data communication with the respective user terminals 400 via the network 50. The communication unit 710 corresponds to a communication device. The control unit 730 to be described later exchanges data with the respective user terminals 400 via the communication unit 710.

The storage unit 720 includes a skill determination result table 720a, a personal information table 720b, and an expert data table 720c. The storage unit 720 corresponds to a storage device such as a semiconductor memory device, for example, a RAM, a ROM, a flash memory, and the like.

The skill determination result table 720a is a table which holds the skill determination result to be notified by the user terminal 400. A data structure of the skill determination result table 720a is the same as the data structure of the skill determination result table 520a illustrated in FIG. 22, for example.

The personal information table 720b is a table which holds the user's personal information. A data structure of the personal information table 720b is the same as the data structure of the personal information table 520b illustrated in FIG. 24, for example.

The expert data table 720c is a table which holds information relating to the expert model data. FIG. 35 is a diagram illustrating an example of a data structure of the expert data table. As illustrated in FIG. 35, the expert data table 720c associates expert identification information, profile information, model data, and an evaluation value with each other. Among them, the expert identification information is information to uniquely identify the expert. The profile information is information of the expert's profile. Examples of the expert profile information include information on the expert's gender, age, weight, height and the like. The model data corresponds to the model data 120a that has been described in the first embodiment.

The control unit 730 includes an acquisition unit 730a, a reception unit 730b, a selection unit 730c, and a notification unit 730d. The control unit 730 corresponds to an integrated device, for example, an ASIC, a FPGA, and the like. In addition, the control unit 730 corresponds to an electronic circuit, for example, a CPU, an MPU, and the like.

The acquisition unit 730a is an acquisition unit which acquires information relating to the skill determination result from the user terminal 400. For example, the information relating to the skill determination result is information in which user identification information, an item, and the skill determination result are associated with each other. The acquisition unit 730a associates the user identification information, the item, and the skill determination result with each other and stores the resultant in the skill determination result table 720a.

When storing the information relating to the skill determination result in the skill determination result table 720a, the acquisition unit 730a adds the information on the skill determination result in a record if the record on the same set of the user identification information and the item has been already stored.

The reception unit 730b executes the following operation when receiving an access request relating to the expert model data from the user terminal. The reception unit 730b displays a display screen in which the expert profile information, the model data, and the evaluation value stored in the expert data table 720c are associated with each other on the user terminal 400. When receiving the selection of the model data from the user who operates the user terminal, the reception unit 730b notifies the user terminal 400 of the model data for which the selection has been received. Incidentally, the notification unit 730d to be described later may notify the user terminal 400 of the model data for which the selection has been received.

In addition, when information on an evaluation value with respect to the expert model data is received from the user terminal 400, the reception unit 730b updates the evaluation value. For example, the reception unit 730b may update the evaluation value of the expert data table 720c by averaging evaluation values from the respective user terminals 400 corresponding to an expert.

Although the description has been given regarding the case where the user operating the user terminal selects the model data in the above-described example, the server 700 may select the model data suitable for the user and notify the user terminal 400 of the selected model data.

The selection unit 730c is a processing unit which selects the model data suitable for the user. For example, the selection unit 730c acquires the user identification information from the user terminal 400 and acquires the gender, the age, the height, and the weight corresponding to the user identification information from the personal information table 720b. In the following description, the gender, the age, the height, and the weight which correspond to the user identification information will be collectively referred to as user profile information if appropriate.

The notification unit 730d is a processing unit which notifies the user terminal 400 serving as a request source of the model data acquired from the selection unit 730c.

Continuously, an example of a process of the selection unit 730c will be described. The selection unit 730c selects the profile information of the expert data table 720c which is the most similar to the user profile information. The selection unit 730c selects the model data of a record corresponding to the selected profile information and outputs the selected model data to the notification unit 730d.

The selection unit 730c may select the similar profile information in any way. For example, the selection unit 730c compares the user profile information and the expert profile information, grants each score depending on whether the gender matches, an age difference, a height difference, and a weight difference, and selects the profile information having the highest total score as the similar profile information. For example, a predetermined score is granted when the genders match each other and the score is not granted when the genders do not match each other. In regard to the age difference, the height difference, and the weight difference, a larger score is granted to the smaller difference.

Further, the selection unit 730c may acquire motion data of the user from the user terminal 400 and acquire the model data, which is the most similar to the acquired motion data, from the model data of the expert data table 720c. For example, the selection unit 730c selects the model data which is the most similar to the motion data of the user through skill determination by performing the same process as that of the skill determination device 100, which has been described in the first embodiment, based on the motion data of the user and the respective model data of the expert data table 720c. For example, the selection unit 730c may perform the skill determination and select the model data with the largest number of "Excellent" as the most similar model data.

In addition, the selection unit 730c may associate the model data of which the user terminal 400 is notified and the skill determination result based on the model data with each other and store the resultant in the skill determination result table 720a. The selection unit 730c determines whether the user's skill has been improved based on the skill determination result stored in the skill determination result table 720a by repeatedly executing the above-described process. For example, the selection unit 730c determines that the user and the expert have good chemistry when the number of "Excellent" increases by comparing the past skill determination result and the current skill determination result that correspond to the same user identification information. In this case, the selection unit 730c continuously notifies the user terminal 400 of the same expert model data. In addition, the selection unit 730c may perform correction to increase the evaluation value of the expert when the number of "Excellent" increases.

On the other hand, the selection unit 730c determines that the user and the expert have bad chemistry when the number of "Excellent" decreases or does not change by comparing the past skill determination result and the current skill determination result that correspond to the same user identification information. In this case, the selection unit 730c notifies the user terminal 400 of another expert model data. In addition, the selection unit 730c may perform correction to decrease the evaluation value of the expert when the number of "Excellent" decreases or does not change.

Figure 36:
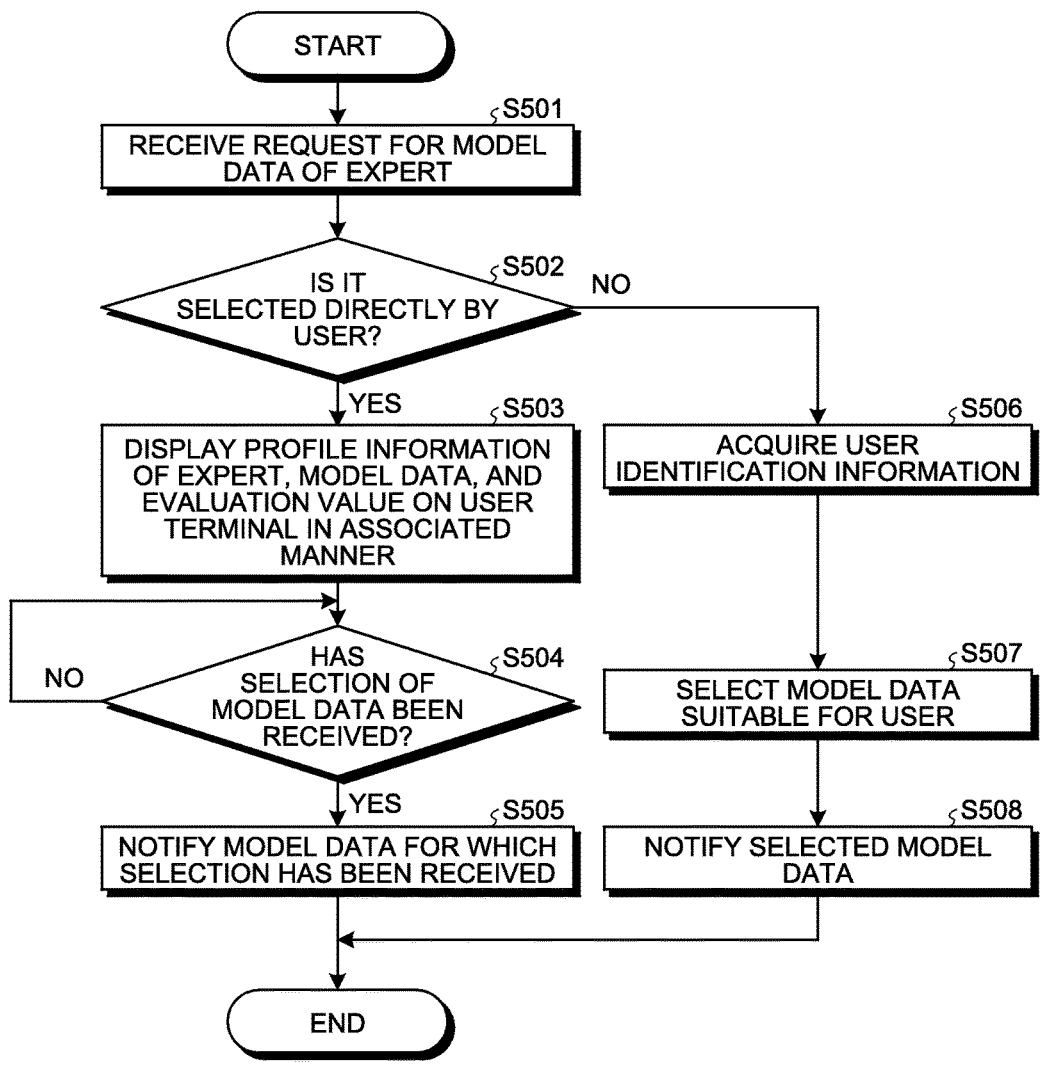
FIG. 36 is a flowchart illustrating a processing procedure of the server according to the fourth embodiment.

Next, an example of a processing procedure of the server 700 according to the fourth embodiment will be described. FIG. 36 is a flowchart illustrating a processing procedure of the server according to the fourth embodiment. As illustrated in FIG. 36, the reception unit 730b of the server 700 receives a request for the expert model data from the user terminal 400 (Step S501).

Here, when the user directly selects the expert model data (Yes in Step S502), the server 700 transitions to Step S503. On the contrary, when the user does not directly select the expert model data (No in Step S502), the server 700 transitions to Step S506.

The subsequent process to Step S503 will be described. The reception unit 730b of the server 700 displays the expert profile information, the model data, and the evaluation value in an associated manner on the user terminal 400 (Step S503).

The reception unit 730b determines whether the selection of the model data has been received (Step S504). When the selection of the model data has not been received (No in Step S504), the reception unit 730b transitions to Step S504 again.

On the other hand, when the selection of the model data has been received (Yes in Step S504), the reception unit 730b notifies the user terminal 400 of the model data for which the selection has been received (Step S505).

The subsequent process to Step S506 will be described. The selection unit 730c of the server 700 acquires the user identification information from the user terminal 400 (Step S506). The selection unit 730c selects the model data suitable for the user (Step S507). The server 700 notifies the user terminal 400 of the model data selected by selection unit 730c (Step S508).

Next, an effect of the server 700 according to the fourth embodiment will be described. The server 700 displays the expert model data on the user terminal 400 and notifies the user terminal 400 of the model data for which the selection has been received when receiving the selection of the expert model data. Alternatively, the server 700 selects the expert model data suitable for the user and notifies the user terminal 400 of the selected expert model data. Thus, the user can perform the skill determination using the expert model data suitable for himself.

According to an embodiment of the invention, generally, it is possible to automatically determine the user's skill.

Figure 37:
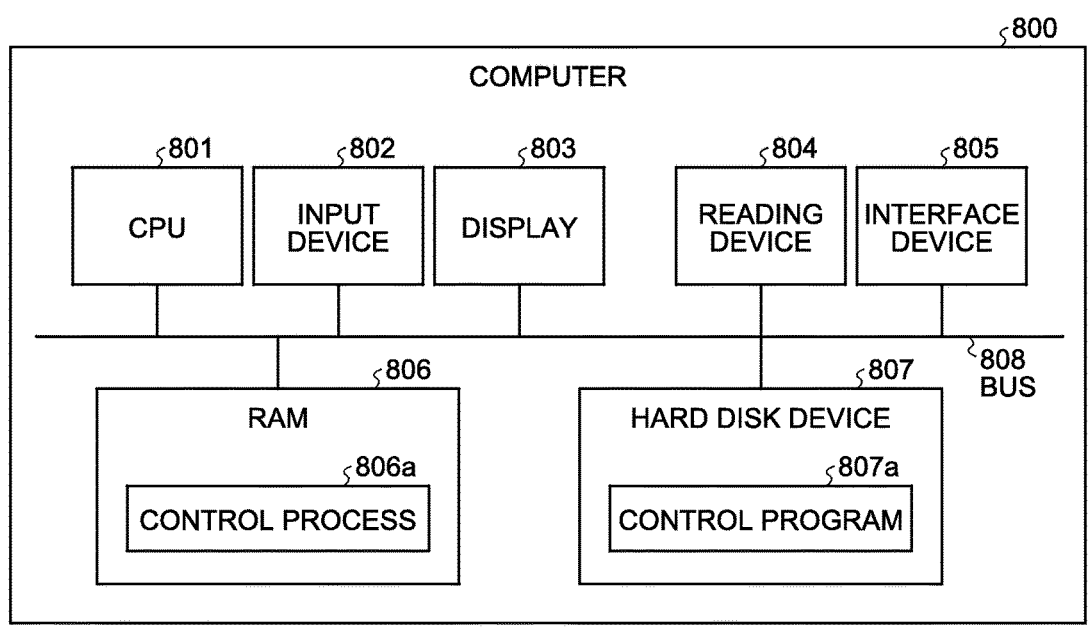
FIG. 37 is a diagram illustrating an example of a computer that executes a control program.

Next, a description will be given regarding an example of a computer that executes a control program which implements the same function as the servers 500, 600 and 700 illustrated in the above-described embodiments and a hardware configuration thereof. FIG. 37 is a diagram illustrating an example of the computer that executes the control program.

As illustrated in FIG. 37, a computer 800 includes a CPU 801 which executes various types of arithmetic processing, an input device 802 which receives input of data from a user, and a display 803. In addition, the computer 800 includes a reading device 804 which reads a program or the like from a storage medium and an interface device 805 which performs exchange of data with another computer via a network. In addition, the computer 800 includes a RAM 806 which temporarily stores various types of information and a hard disk device 807. Further, the respective devices 801 to 807 are connected to a bus 808.

The hard disk device 807 includes a control program 807a. The CPU 801 reads the control program 807a and load the program on the RAM 806. The control program 807a functions as a control process 806a. For example, the control process 806a corresponds to the acquisition unit 530a, the reception unit 530b, the retrieval unit 530c, and the screen generation unit 530d illustrated in FIG. 21. Alternatively, the control process 806a corresponds to the acquisition unit 630a, the classification unit 630b, and the SNS providing unit 630c illustrated in FIG. 29. Alternatively, the control process 806a corresponds to the acquisition unit 730a, the reception unit 730b, the selection unit 730c, and the notification unit 730d illustrated in FIG. 34.

Incidentally, the control program 807a is not necessarily stored in the hard disk device 807 from the beginning. For example, the respective programs may be stored in "portable the physical media", such as a flexible disk (FD), a CD-ROM, the DVD disk, a magneto-optical disk, and an IC card, which are inserted into the computer 800. Then, the computer 800 may be configured to read and execute the control program 807a.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

The invention claimed is:

1. A non-transitory computer-readable recording medium having stored therein a skill determination program that causes a computer to execute a process comprising:
calculating each degree of similarity between each position information of a feature point of a plurality of first frames and position information of a feature point of a second frame to obtain a plurality of degrees of similarity, where the feature point of each of the first frames corresponds to a predetermined part or a joint of a body of a first user and the feature point of the second frame corresponds to the predetermined part or the joint of the body of a second user;
identifying a selected first frame, among the plurality of first frames, that corresponds to the second frame based on a degree of similarity from the plurality of degrees of similarity;
comparing a first time of the selected first frame with a second time of a previously selected first frame which has already been matched to a previous second frame;
setting a weight of the selected first frame to a first value when the first time is after the second time and a difference between the first time and the second time is within a predetermined range;
setting the weight to a second value lower than the first value when the first time is after the second time and the difference between the first time and the second time is not within the predetermined range;
setting the weight to a third value lower than the second value when the first time is before the second time;
correcting the degree of similarity using the weight;
re-identifying the selected first frame, among the plurality of first frames based on the degree of similarity, when the degree of similarity has been corrected;
specifying a phase type corresponding to the selected first frame as a type of the second frame, where the plurality of first frames have a plurality of phase types;
generating a plurality of modules which determine a feature amount of a motion of the second user from the feature point included in the second frame, where the modules respectively correspond to the phase types;
selecting one of the modules corresponding to the phase type of the second frame;
outputting the second frame to the one of the modules selected.

2. The non-transitory computer-readable recording medium according to claim 1, wherein
the modules output a skill determination result, and
the process further comprises outputting the skill determination result using image information, voice information or physical stimulation with respect to the second user.

3. A skill determination method comprising:
calculating each degree of similarity between each position information of a feature point of a plurality of first frames and position information of a feature point of a second frame to obtain a plurality of degrees of similarity, where the feature point of each of the first frames corresponds to a predetermined part or a joint of a body of a first user and the feature point of the second frame corresponds to a predetermined part or a joint of a body of a second user, using a processor;
identifying a selected first frame, among the plurality of first frames, that corresponds to the second frame based on a degree of similarity from the plurality of degrees of similarity, using the processor;
comparing a first time of the selected first frame with a second time of a previously selected first frame which has already been matched to a previous second frame;
setting a weight of the selected first frame to a first value when the first time is after the second time and a difference between the first time and the second time is within a predetermined range;
setting the weight to a second value lower than the first value when the first time is after the second time and the difference between the first time and the second time is not within the predetermined range;
setting the weight to a third value lower than the second value when the first time is before the second time;
correcting the degree of similarity using the weight;
re-identifying the selected first frame, among the plurality of first frames based on the degree of similarity, when the degree of similarity has been corrected, using the processor;
specifying a phase type corresponding to the selected first frame as a type of the second frame, where the plurality of first frames have a plurality of phase types, using the processor;
generating a plurality of modules which determine a feature amount of a motion of the second user from the feature point included in the second frame, where the modules respectively correspond to the phase types;
selecting one of the modules corresponding to the phase type of the second frame;
outputting the second frame to the one of the modules selected, using the processor.

4. A skill determination device comprising:
a processor that executes a process comprising:
calculating each degree of similarity between each position information of a feature point of a plurality of first frame and position information of a feature point of a second frame to obtain a plurality of degrees of similarity, where the feature point of each of the first frames corresponds to a predetermined part or a joint of a body of a first user and the feature point of the second frame corresponds to a predetermined part or a joint of a body of a second user;
selecting the first frame that corresponds to the second frame based on a degree of similarity from the plurality of degrees of similarity;
comparing a first time of the selected first frame with a second time of a previously selected first frame which has already been matched to a previous second frame;
setting a weight of the selected first frame to a first value when the first time is after the second time and a difference between the first time and the second time is within a predetermined range;
setting the weight to a second value lower than the first value when the first time is after the second time and the difference between the first time and the second time is not within the predetermined range;
setting the weight to a third value lower than the second value when the first time is before the second time;
correcting the degree of similarity using the weight;
re-selecting the selected first frame, among the plurality of first frames based on the degree of similarity, when the degree of similarity has been corrected;
specifying a phase type corresponding to the selected first frame as a type of the second frame, where the plurality of first frames have a plurality of phase types;

generating a plurality of modules which determine a feature amount of a motion of the second user from the feature point included in the second frame, where the modules respectively correspond to the phase types;

selecting one of the modules corresponding to the phase type of the second frame;

outputting the second frame to the one of the modules selected.

5. A system comprising:

a skill determination device, including a first processor that executes a process comprising:

calculating each a degree of similarity between each position information of a feature point of a plurality of first frames and position information of a feature point of a second frame to obtain a plurality of degrees of similarity, where the feature point of each of the first frames corresponds to a predetermined part or a joint of a body of a first user and the feature point of the second frame corresponds to the predetermined part or the joint of the body of a second user;

identifying a selected first frame, among the plurality of first frames, that corresponds to the second frame based on a degree of similarity from the plurality of degrees of similarity;

comparing a first time of the selected first frame with a second time of a previously selected first frame which has already been matched to a previous second frame;

setting a weight of the selected first frame to a first value when the first time is after the second time and a difference between the first time and the second time is within a predetermined range;

setting the weight to a second value lower than the first value when the first time is after the second time and the difference between the first time and the second time is not within the predetermined range;

setting the weight to a third value lower than the second value when the first time is before the second time;

correcting the degree of similarity using the weight;

re-identifying the selected first frame, among the plurality of first frames based on the degree of similarity, when the degree of similarity has been corrected;

specifying a phase type corresponding to the selected first frame as a type of the second frame where the plurality of first frames have a plurality of phase types;

generating a plurality of modules which determine a feature amount of a motion of the second user from the feature point included in the second frame, where the modules respectively correspond to the phase types and output a skill determination result;

selecting one of the modules corresponding to the phase type of the second frame, and outputting the second frame to the one of the modules selected; and a server, including a second processor that executes a process comprising:

acquiring the skill determination result, obtained when a user performs a motion relating to a predetermined item, from the skill determination device;

storing the predetermined item and the skill determination result in a storage unit in an associated manner;

retrieving notification information relating to the skill determination result based on the predetermined item corresponding to the skill determination result and a first correspondence information which stores the predetermined item and notification information relating to the predetermined item in an associated manner, when receiving access with respect to the skill determination result from the skill determination device;

retrieving the product information corresponding to a feature of the skill determination result based on the feature of the skill determination result and second correspondence information of the feature of the skill determination result and the product information stored in an associated manner; and generating a screen, which includes the skill determination result serving as a target of the access and the notification information and the product information retrieved, and notifies the skill determination device serving as a source of the access of information on the generated screen.

6. A system comprising:

a skill determination device, including a first processor that executes a process comprising:

calculating each degree of similarity between each position information of a feature point of a plurality of first frames and position information of a feature point of a second frame to obtain a plurality of degrees of similarity, where the feature point of each of the first frames corresponds to a predetermined part or a joint of a body of a first user and the feature point of the second frame corresponds to the predetermined part or the joint of the body of a second user;

identifying a selected first frame, among the plurality of first frames, that corresponds to the second frame based on a degree of similarity from the plurality of degrees of similarity;

comparing a first time of the selected first frame with a second time of a previously selected first frame which has already been matched to a previous second frame;

setting a weight of the selected first frame to a first value when the first time is after the second time and a difference between the first time and the second time is within a predetermined range;

setting the weight to a second value lower than the first value when the first time is after the second time and the difference between the first time and the second time is not within the predetermined range;

setting the weight to a third value lower than the second value when the first time is before the second time;

correcting the degree of similarity using the weight;

re-identifying the selected first frame, among the plurality of first frames based on the degree of similarity, when the degree of similarity has been corrected;

specifying a phase type corresponding to the selected first frame as a type of the second frame, where the plurality of first frames have a plurality of phase types;

generating a plurality of modules which determine a feature amount of a motion of the second user from the feature point included in the second frame, where the modules respectively correspond to the phase types and output a skill determination result;

selecting one of the modules corresponding to the phase type of the second frame, and outputting the second frame to the one of the modules selected; and a server device, including a second processor that executes a process comprising:
classifying user identification information into groups for each feature of a user based on correspondence information which stores the user identification information to identify the user and the feature of the user in an associated manner; and
specifying a group to which received user identification information belong, when a skill determination result and the user identification information with respect to the user is received from the skill determination device, among the respective groups; and
notifying the skill determination result to a user terminal corresponding to the user identification information included in the specified group.

7. A system comprising:
a skill determination device, including a first processor that executes a process comprising:
calculating each degree of similarity between each position information of a feature point of a plurality of first frames and position information of a feature point of a second frame to obtain a plurality of degrees of similarity, where the feature point of each of the first frames corresponds to a predetermined part or a joint of a body of a first user and the feature point of the second frame corresponds to a predetermined part or a joint of a body of a second user;
identifying a selected first frame, among the plurality of first frames, that corresponds to the second frame based on a degree of similarity from the plurality of degrees of similarity;
comparing a first time of the selected first frame with a second time of a previously selected first frame which has already been matched to a previous second frame;
setting a weight of the selected first frame to a first value when the first time is after the second time and a difference between the first time and the second time is within a predetermined range;
setting the weight to a second value lower than the first value when the first time is after the second time and the difference between the first time and the second time is not within the predetermined range;
setting the weight to a third value lower than the second value when the first time is before the second time;
correcting the degree of similarity using the weight;
re-identifying the selected first frame, among the plurality of first frames based on the degree degrees of similarity, when the degree of similarity has been corrected;
specifying a phase type corresponding to the selected first frame as a type of the second frame, where the plurality of first frames have a plurality of phase types;
generating a plurality of modules which determine a feature amount of a motion of the second user from the feature point included in the second frame, where the modules respectively correspond to the phase types and output a skill determination result;
selecting one of the modules corresponding to the phase type of the second frame; and
outputting the second frame to the one of the modules selected; and
a server, including
a memory; and
a second processor that executes a process comprising:
storing a plurality of types of information in the memory, the plurality of types of information being information in which features of first users and motion information, obtained when the first users make a motion relating to a predetermined item, are associated with each other, respectively,
notifying the skill determination device of a plurality of features of the first users;
acquiring motion information corresponding to a feature of a selected first user from the memory when any of the features of the selected first user is selected among the plurality of features of the first users;
notifying the skill determination device of the motion information acquired by the acquiring; and
determining a skill of the second user based on the motion information.

* * * * *